US010722491B2

(12) United States Patent
Ochoa Rodríguez et al.

(10) Patent No.: US 10,722,491 B2
(45) Date of Patent: Jul. 28, 2020

(54) PHENOL COMPOUND AND COMBINATION OF SAME WITH A BENZODIAZEPINE FUSED TO 1,4-DIHYDROPYRIDINE FOR TREATING DISEASES OF THE CENTRAL NERVOUS AND VASCULAR SYSTEMS

(71) Applicants: UNIVERSIDAD DE LA HABANA, Havana (CU); CENTRO DE INVESTIGACIÓN Y DESARROLLO DE MEDICAMENTOS CIDEM, Havana (CU)

(72) Inventors: Estael Ochoa Rodríguez, Havana (CU); Yamila Verdecia Reyes, Havana (CU); Yanier Núñez Figueredo, Havana (CU); Jeney Ramírez Sánchez, Havana (CU); Maylin Wong Guerra, Havana (CU); Luis Arturo Fonseca Fonseca, Havana (CU); Gilberto Lázaro Pardo Andreu, Havana (CU); Claudia Amanda Canaán-Haden Navarro, Havana (CU); Abel Mondelo Rodríguez, Havana (CU); Pedro Gilberto Bárzaga Fernández, Havana (CU); Nicté González Alfonso, Havana (CU); René Delgado Hernández, Havana (CU); Alejandro Saúl Padrón Yaquis, Havana (CU)

(73) Assignees: UNIVERSIDAD DE LA HABANA, Havana (CU); CENTRO DE INVESTIGACIÓN Y DESARROLLO DE MEDICAMENTOS CIDEM, Havana (CU)

( * ) Notice: Subject to any disclaimer, the term of this patent is extended or adjusted under 35 U.S.C. 154(b) by 0 days.

(21) Appl. No.: 16/098,683

(22) PCT Filed: May 3, 2017

(86) PCT No.: PCT/CU2017/050003
§ 371 (c)(1),
(2) Date: Nov. 2, 2018

(87) PCT Pub. No.: WO2017/190714
PCT Pub. Date: Nov. 9, 2017

(65) Prior Publication Data
US 2019/0133996 A1    May 9, 2019

(30) Foreign Application Priority Data
May 4, 2016   (CU) .................................. 2016-0059

(51) Int. Cl.
| | | |
|---|---|---|
| A61K 31/357 | (2006.01) |
| A61K 31/5513 | (2006.01) |
| A61K 9/20 | (2006.01) |
| A61K 9/14 | (2006.01) |
| A61K 47/06 | (2006.01) |
| A61K 9/08 | (2006.01) |
| A61K 47/44 | (2017.01) |
| A61K 9/00 | (2006.01) |
| A61K 9/10 | (2006.01) |
| C07D 319/06 | (2006.01) |
| A61K 31/366 | (2006.01) |
| A61P 9/10 | (2006.01) |
| A61P 25/28 | (2006.01) |
| A61P 25/16 | (2006.01) |

(52) U.S. Cl.
CPC ............ *A61K 31/357* (2013.01); *A61K 9/006* (2013.01); *A61K 9/0019* (2013.01); *A61K 9/08* (2013.01); *A61K 9/10* (2013.01); *A61K 9/14* (2013.01); *A61K 9/2018* (2013.01); *A61K 9/2059* (2013.01); *A61K 31/366* (2013.01); *A61K 31/5513* (2013.01); *A61K 47/06* (2013.01); *A61K 47/44* (2013.01); *A61P 9/10* (2018.01); *A61P 25/16* (2018.01); *A61P 25/28* (2018.01); *C07D 319/06* (2013.01)

(58) Field of Classification Search
CPC .................................................... A61K 31/357
USPC ......................................................... 549/274
See application file for complete search history.

(56) References Cited

FOREIGN PATENT DOCUMENTS

JP    2007063444 A    3/2007

OTHER PUBLICATIONS

Nunez-Figueredo et al., Eur. J. Pharm. (2014), 77, pp. 57-65.*
Vivier et al., "Development of the First Two-Pore Domain Potassium Channel TREK-1 (TWIK-Related K Channel 1)—Selective Agonist Possessing in Vivo Anti-Nociceptive Activity", Journal of Medicinal Chemistry, vol. 60., No. 3, pp. 1076-1088 (2017).
Buendia et al., "Nrf2-ARE Pathway: An Emerging Target Against Oxidative Stress and Neuroinflammation in Neurodegenerative Diseases", Pharmacology and Therapeutics, vol. 157, 23, pp. 84-104 (2015).

(Continued)

*Primary Examiner* — Taofiq A Solola
(74) *Attorney, Agent, or Firm* — Hoffmann & Baron, LLP

(57) ABSTRACT

The present invention relates to Chemistry, Pharmaceutical and in particular to the preparation of formulations from derivatives of phenolic or polyphenolic compounds and from derivatives of phenolic or polyphenolic compounds combined with tricyclic systems of the benzodiazepine type fused to derivatives of 1,4-dihydropyridines with action on the Central Nervous and Vascular Systems.
These pharmaceutical compositions exhibit GABAergic, antiglutamatergic, calcium channel modulating, mitoprotective, anti-oxidant, anti-inflammatory, and antiapoptotic action, usable in the treatment of cardiovascular, cerebrovascular, neurodegenerative, neuropsychiatric and neurological diseases.

15 Claims, 16 Drawing Sheets

(56) References Cited

OTHER PUBLICATIONS

Sandhu et al., "Synthesis and Biological Evaluation of Arylidene Analogues of Meldrum's Acid as a New Class of Antimalarial and Antioxidant Agents", Bioorganic & Medicinal Chemistry, Pergamon, GB, vol. 18, No. 15, pp. 5626-5633 (2010).
International Search Report for corresponding International Application No. PCT/CU2007/050003, pp. 1-3 (Aug. 14, 2017).

* cited by examiner

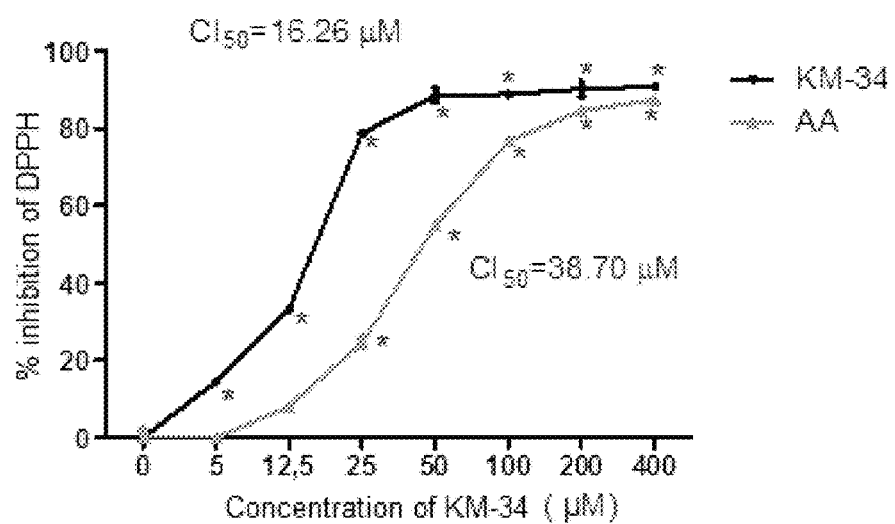
Figure 1. Percentage reduction of DPPH (100 µM) by KM-34 (5-400 µM) was determined by changing the absorbance at 550 nm from a target containing only DPPH and vehicle (zero concentration of KM-34 or AA), after 30 minutes of reaction. Values are expressed as the mean ± SD (n = 3). * P <0.05 with respect to the vehicle.

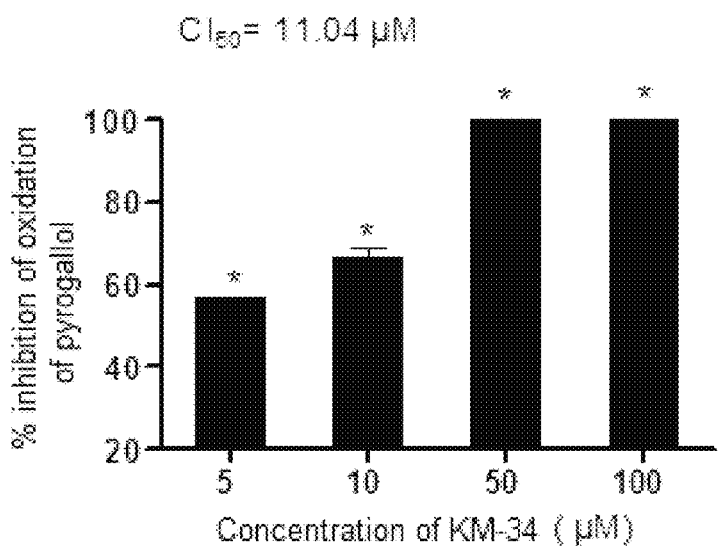

Figure 2 Activity of KM-34 (5-100 µM) as radical scavenger O2.- expressed as the percentage inhibition of autoxidation of pyrogallol. The same was obtained by varying the absorbance at 420 nm for 1 minute with respect to a blank (uninhibited reaction, without KM-34; the slope was calculated for each concentration of the sample and for the target with a $R^2 > 0.98$. The reaction takes place in 50 mM Tris-HCl pH 8.2 buffer and was initiated by the addition of 0.134 mM Pirogalol * $P < 0.05$ to the carrier (uninhibited reaction).

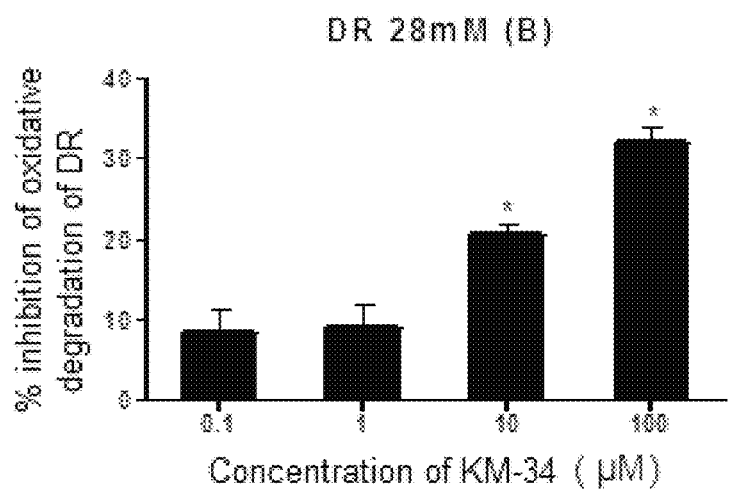

Fig.3. Effect of KM-34 (0.1, 1.10, 100 µM) on oxidative damage to 2.8 (A) and 28 mM (B) DR respectively, induced by Fe3 + - EDTA and ascorbate. The solutions were incubated 30 minutes at 37 ° C and contained 10 mM phosphate buffer pH 7.4, 100 µM EDTA, 25 µM FeCl3, DR (2.8 or 28 mM). Reactions were initiated with 100 µM AA. The results are expressed as the percent inhibition of DR degradation relative to a control containing only absolute ethanol, obtained by changes in absorbance at 532 nm. The bars show the mean ± SD (n = 3). * P <0.05 with respect to control.

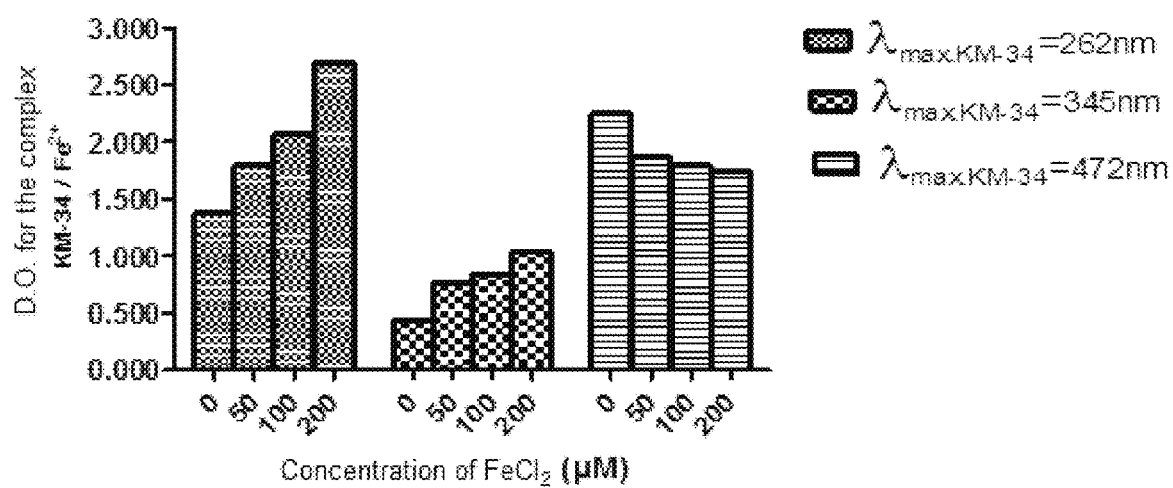
Fig.4 Maximum absorption data on UV-VIS (200-500nm) of the 100 μM KM-34 in a mixture of 10 mM phosphate buffer (KH2PO4 / KOH) pH 7.4 and absolute ethanol 14: 1 (v: v) and The absorbance in the presence of FeCl2 (50,100 and 200 μM) dissolved in 10mM HCL.

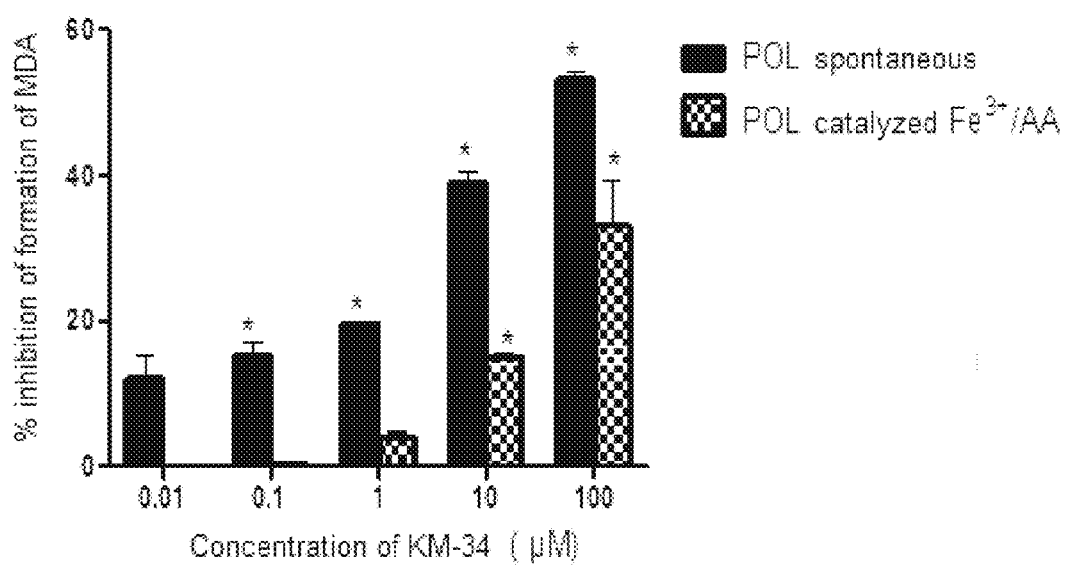
Fig.5 Effects of KM-34 (0.01-100 μM) on spontaneous lipid peroxidation and e induced by 100 mM FeCl3 and 100 mM AA. The control contains absolute ethanol instead of KM-34. The samples were incubated at 37 °C for 1 hour and then the MDA levels were quantified by thiobarbituric acid (ATB) and the absorbance was determined at 532 nm. Values are expressed as the mean ± SD (n = 3). * P <0.05 with respect to the control.

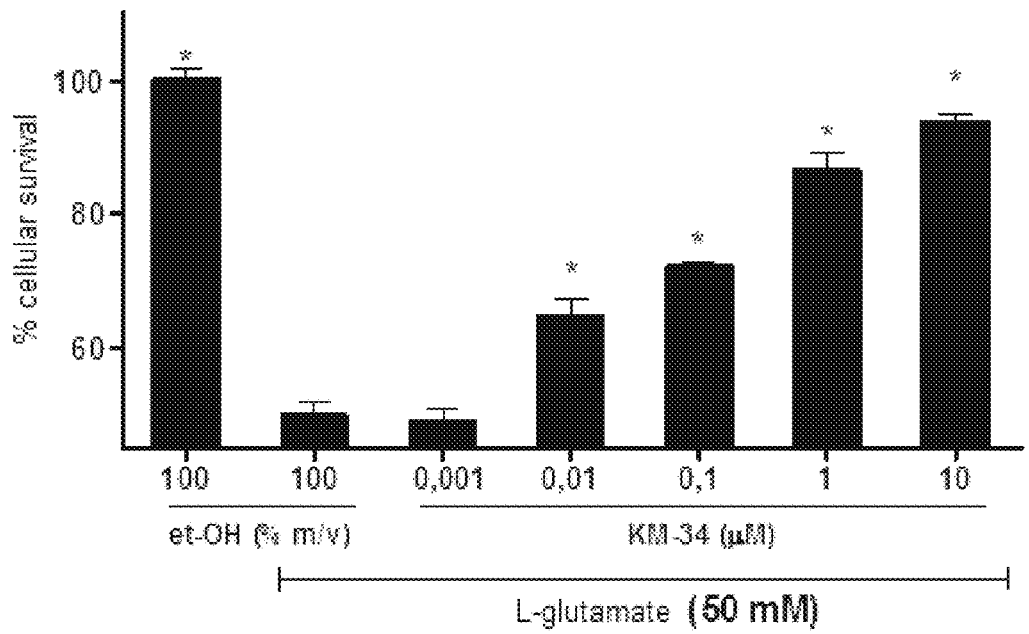

Fig.6. Cytoprotective effect of KM-34 (0.001-10 µM) against damage induced by L-glutamate (50 mmol / L) in cultures of PC12 cells. Viability (% live cells) was determined by the MTT assay. Cells were seeded at a density of 5 x 105 cells / mL in a 96-well plate. KM-34 was added simultaneously to the addition of L-glutamate. The culture was then allowed to incubate at 37 ° C, 95% $O_2$ and 5% $CO_2$ for 4 hours. After this time the supernatant was removed and the cells were incubated with 20 µg of MTT for an additional 2 hours and the absorbance at 450 nm was measured with reference to 630 nm. The results are expressed as percentage of live cells relative to the control (cells without damage, 100% of live cells. * Represents significant differences ($p < 0.05$) with respect to the L-glutamate control.

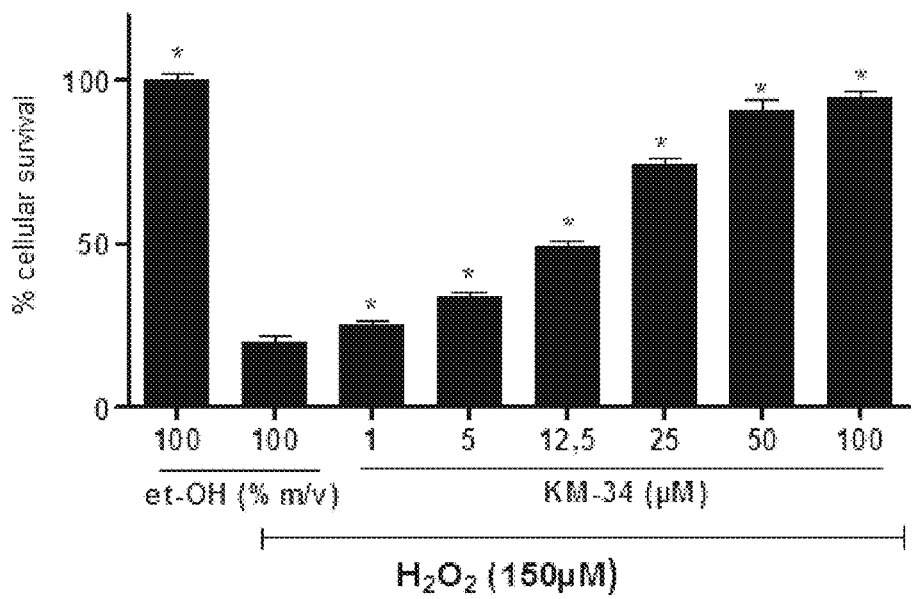

Fig.7. Cytoprotective effect of KM-34 (1-100 µM) against damage induced by H2O2 (150 µM) in cultures of PC12 cells. Viability (% live cells) was determined by the MTT assay. Cells were seeded at a density of 5 x 105 cells / mL in a 96-well plate. The KM-34 was added simultaneously to the addition of the H2O2 mixture. The culture was then allowed to incubate at 37 ° C, 95% O 2 and 5% CO 2 for 4 hours. After this time the supernatant was removed and the cells were incubated with 20 µg of MTT for an additional 2 hours and the absorbance at 450 nm was measured with reference to 630 nm. The results are expressed as percentage of live cells relative to the control (undamaged cells, 100% live cells). The * represents significant differences (p <0.05) with respect to the H2O2 control.

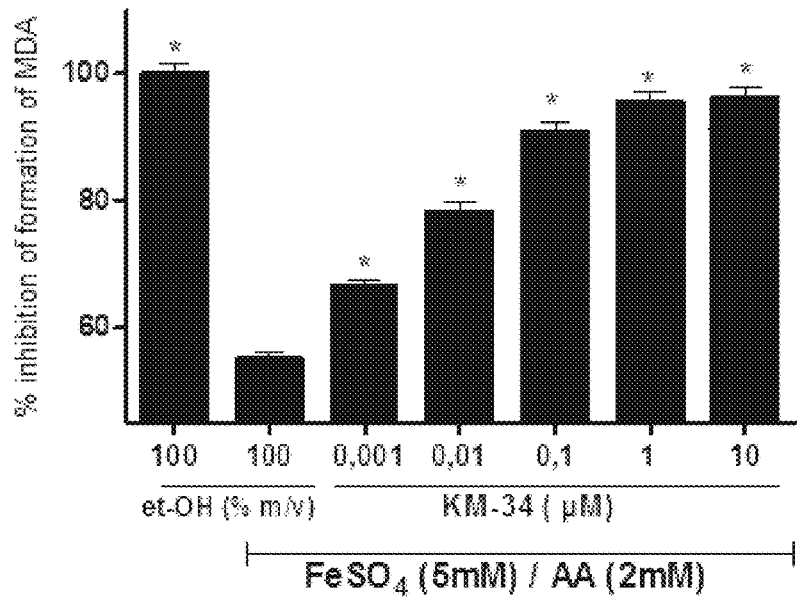

Fig.8. Cytoprotective effect of KM-34 (0.001-10μM) against damage induced by FeSO4 (5 mmol / L) and ascorbic acid (AA, 2 mmol / L) in cultures of PC12 cells. Viability (% live cells) was determined by the MTT assay. Cells were seeded at a density of 5 x 105 cells / mL in a 96-well plate. The KM-34 was added simultaneously to the addition of the mixture of FeSO 4 and AA. The culture was then allowed to incubate at 37 ° C, 95% O 2 and 5% CO 2 for 4 hours. After this time the supernatant was removed and the cells were incubated with 20 μg of MTT for a further 2 hours and the absorbance at 450 nm was measured with reference to 630 nm. The results are expressed as percentage of live cells relative to the control (undamaged cells, 100% live cells. * Represents significant differences ($p < 0.05$) with respect to FeSO4 / AA control.

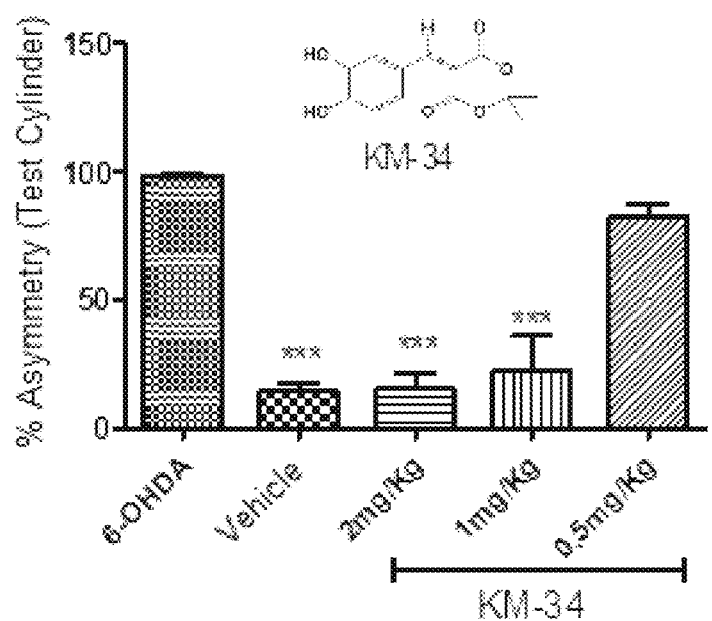

Fig. 9 Effect of KM-34 on damaged animals with 6-OHDA, cylinder test. The graph shows the different treatment groups, evaluated 7 days after the damage. In this case, the neuroprotective capacity of the doses of 2mg and 1mg in the Parkinson's model was observed, as there were statistically significant differences with respect to the animals without treatment. Not being so for the dose of 0.5mg, when not presenting statistically significant differences with respect to the damaged animals without treatment. The values represent the mean percentage of asymmetry, relative to the control group damaged ± SD. Data were analyzed using statistical methods ANOVA and Tukey's * $p < 0.05$.

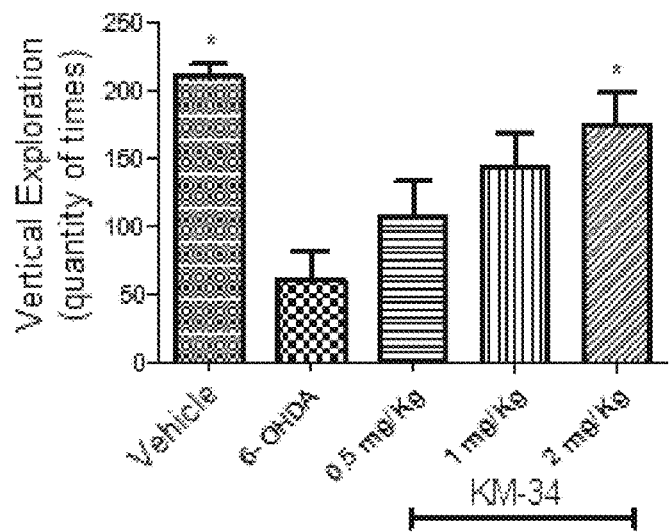

Fig. 10 Effect of KM-34 on animals damaged with 6-OHDA, exploratory behavior. . The graph shows the different treatment groups, evaluated 7 days after the damage. Here the vertical scan values of the different treatment groups are shown. The damaged group has a significantly lower vertical scan than the vehicle control (healthy animals). As the doses of KM-34 are increased, a tendency to increase vertical exploration is observed, being for the group treated with the highest dose statistically significant with respect to the damaging control. The values represent the mean percentage of asymmetry, relative to the control group damaged ± SD. Data were analyzed using statistical methods ANOVA and Tukey's * $p < 0.05$. The results indicate a potential neuroprotective effect of KM34 in Parkinson's disease.

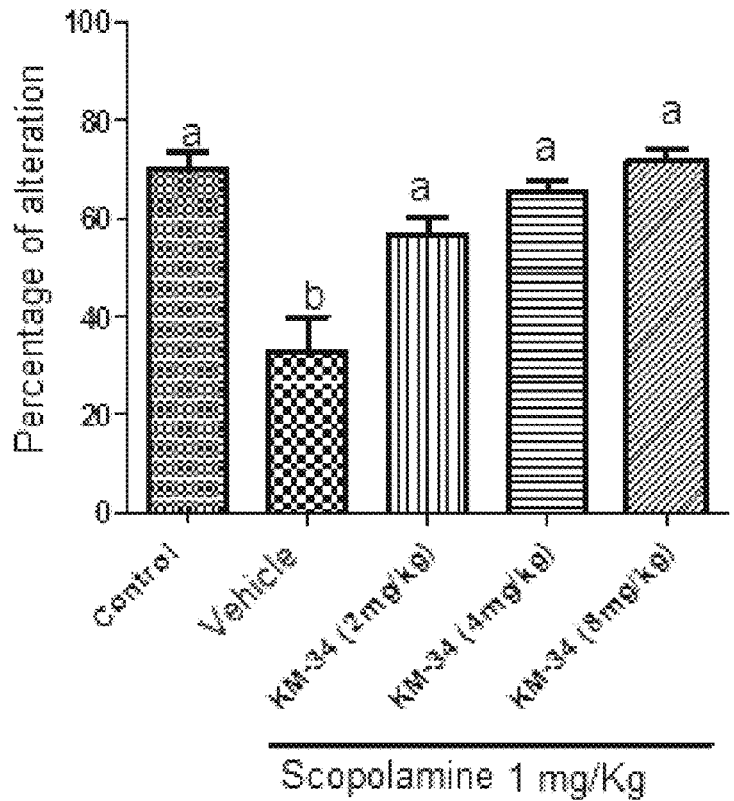
Figure 11: Effect of KM-34 on spatial memory. In the T labyrinth, KM-34 (2, 4 and 8mg / kg, p.o) was given 1 hour prior to scopolamine (1 mg / kg, i.p.). Data are expressed as mean ± SD (n = 7, per group) of the percentage of spontaneous alternation. For statistical analysis, ANOVA and Tukey's multiple comparison test were performed. Different letters differ from each other for p <0.01.

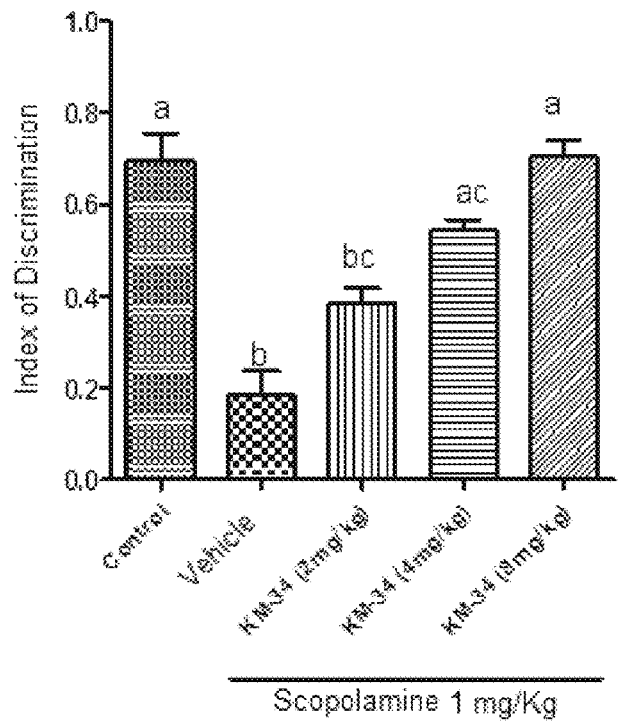

Figure 12: Effect of KM-34 on the recognition memory of new objects. In the new-object recognition test, KM-34 (2, 4 and 8mg / kg, p.o) was administered 1 hour prior to scopolamine (1 mg / kg, i.p.) prior to the training phase. The results are expressed as the discrimination rate of the total time by scanning the object N with respect to F. The data are expressed as mean ± SD (n = 8, per group). For statistical analysis, ANOVA and Tukey's multiple comparison test were performed. Different letters differ from each other for $p < 0.01$.

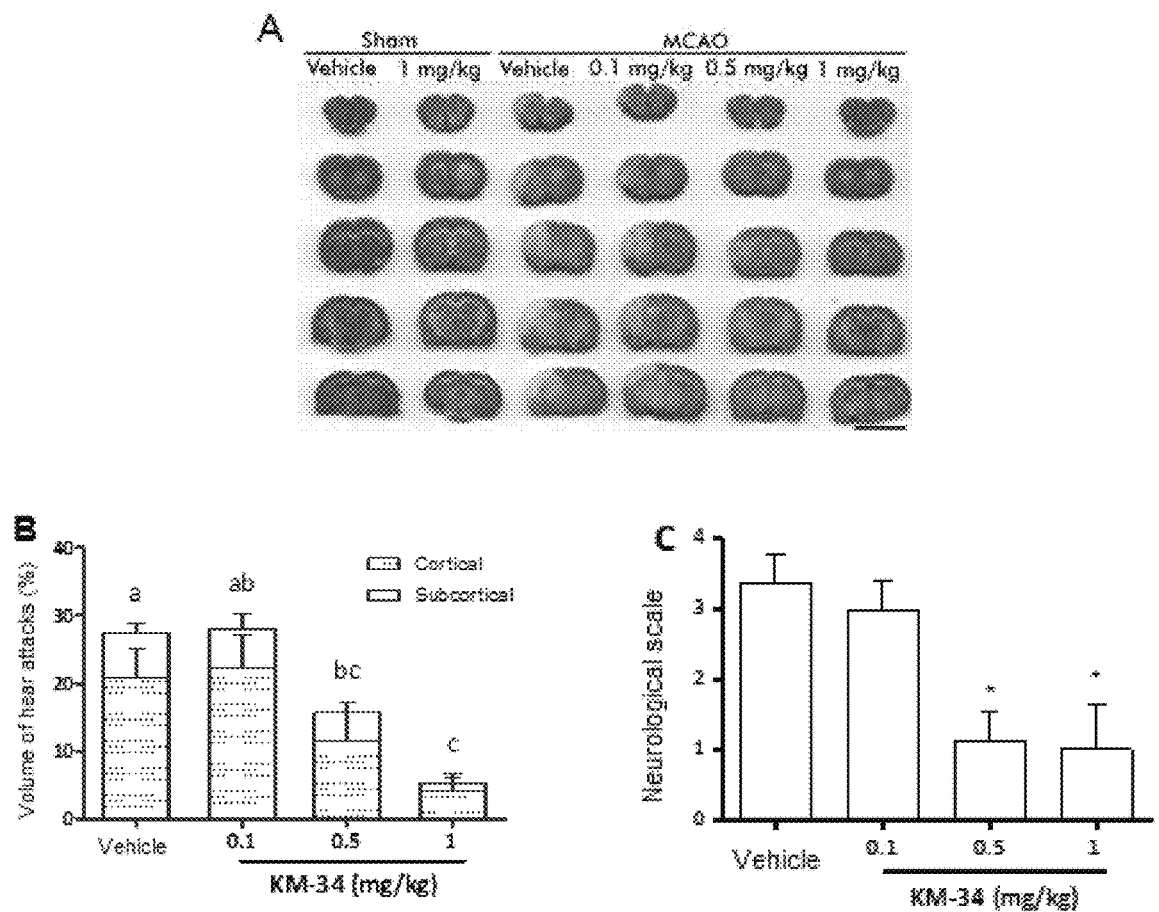

Figure 13. Acute treatment with KM-34 reduced the volume of infarction, edema and deficit in rat behavior after 90 min of middle cerebral artery occlusion (MACA) and 23 hours of reperfusion. The different doses of the compound were administered orally 1 hour after reperfusion. (A) Representative brain coronal sections (2 mm thick) of the sham and ischemic groups treated with vehicle or KM-34 (0.1, 0.5 or 1 mg / kg) and stained with 2,3,5-triphenyltetrazolium (TTC ) 2 %. The red regions correspond to undamaged tissue and white to ischemic regions. (B) Quantitative analysis of cortical, subcortical and total lesion size. (C) Neurological deficit. The bars represent the mean ± SEM (n = 8). Different letters in (A) and * in (B); $p < 0.05$, by ANOVA and post hoc of Newman-Keuls. Scale = 10 mm.

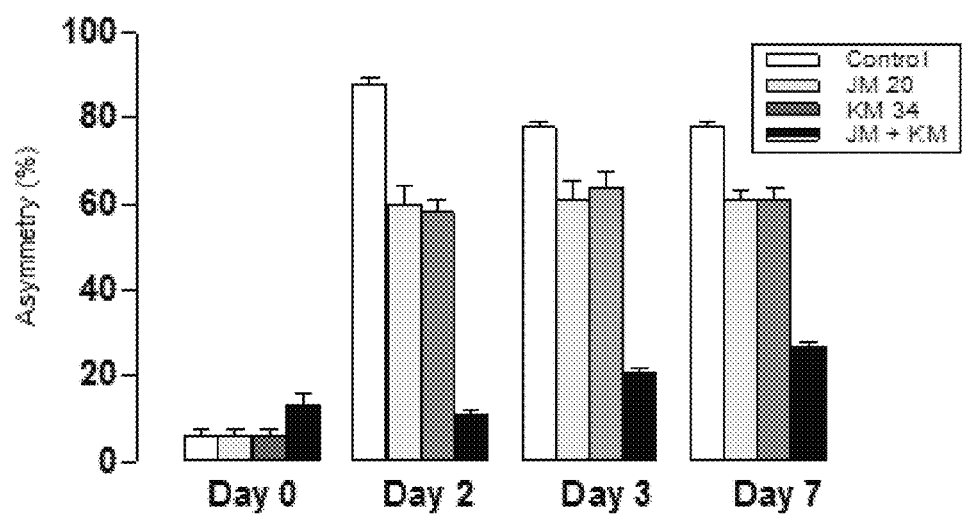
Figure 16. Effect of JM-20, KM-34 and its combination on thermocoagulation-induced asymmetry of cortical arteries

PHENOL COMPOUND AND COMBINATION OF SAME WITH A BENZODIAZEPINE FUSED TO 1,4-DIHYDROPYRIDINE FOR TREATING DISEASES OF THE CENTRAL NERVOUS AND VASCULAR SYSTEMS

This application is the U.S. National Phase of, and Applicant claims priority from, International Patent Application Number PCT/CU2017/050003 filed 3 May 2017, which claims priority from CU 2016-0059 filed 4 May 2016, each of which is incorporated herein by reference.

FIELD OF THE INVENTION

The present invention relates to Chemistry, Pharmaceutical and in particular to the preparation of formulations from phenolic or polyphenolic compound derivatives and from derivatives of phenolic or polyphenolic compounds combined with tricyclic systems of the benzodiazepine type fused to derivatives of 1,4 Dihydropyridines with action on the Central Nervous and Vascular System.

BACKGROUND OF THE INVENTION

In the case of diseases of multifactorial origin such as cardiovascular, cerebrovascular, neurodegenerative, neuropsychiatric and neurological, a single medication is not enough to treat them effectively, so a multiple medication therapy should be used. There are two main reasons for the absence of drugs for the treatment of these diseases: 1) drugs targeting a single pathological mechanism and 2) use of high doses that increases the risk of adverse reactions.

Neurodegeneration is a common theme of many diseases of the nervous system and disorders such as dementia, Alzheimer's disease (AD), Parkinson's disease (PD). These diseases are devastating and expensive to manage, while current treatments are inadequate. The urgency of this problem is compounded by the fact that the incidence of these age-related diseases is increasing rapidly due to the demographic changes that are occurring.

The progressive aging of the world population brings with it the unwanted consequence of an increase in neurodegenerative diseases and senile dementias.

PD is a neurodegenerative disease, with symptoms of motor dysfunction: slow movements, rigidity, resting tremor and alterations in balance. As the disease progresses, many patients develop non-motor symptoms, including anxiety, depression, constipation, and dementia.

These characteristics are attributed to a large reduction in the striatal content of dopamine and to a loss of dopaminergic neurons in the substantia nigra pars compacta (Gauthier, 1982).

Clinical signs of PD appear after dopaminergic neuronal death exceeds a threshold of 70-80% and a loss of striatal nerve endings exceeding 50-60% (Agid, 1991).

Investigations of the developmental mechanisms of PD have indicated that the loss of dopaminergic neurons in the nigra pars substance compact is related to the mitochondrial-I complex deficit (Jenner 1998).

Although there are drugs that relieve Parkinson's symptoms, the chronic use of these drugs is not effective in preventing the progression of PD and has been associated with debilitating side effects. It is therefore of great interest to develop neuroprotective therapies that delay or even stop the degenerative progression.

Worldwide, an estimated 46.8 million people live with dementia. This number is estimated to increase almost twice every 20 years; to 74.7 million in 2030 and 131.5 million by 2050. Dementia also has a huge economic impact. Today, the estimated total worldwide cost of dementia is $818 trillion, and it will be a trillion dollar disease by 2018; with a huge impact on the quality of life of patients and their families and caregivers (Alzheimer's Disease International, World Alzheimer Report 2015. London: Alzheimer's Disease International, 2015)

Of all of them, AD is the most prevalent with about 35 million people suffering from the disease and it is estimated that its incidence will increase significantly in the next three decades, along with the increase in the average age of the population (Reitz, C. Brayne, C. Mayeux, R. Epidemiology of Alzheimer's disease, Nat. Rev. Neurol., 2011, 7, 137-152) (Reitz, C., Mayeux, R. Alzheimer disease: Epidemiology, diagnostic criteria, Risk factors and biomarkers, Biochem, Pharmacol., 2014, 88, 640-651).

AD, is a neurodegenerative disorder of the brain that leads to slow progression of memory and cognitive functions; often accompanied by behavioral alterations such as aggression and depression (Querfurth, H. W., LaFerla, F. M. Alzheimer's disease, N. Engl. J. Med., 2010, 362, 329-344). In its last stage it leaves the patient in bed, incontinent and dependent on care and custody, which is very expensive for the relatives. Death occurs, on average, 9 years after diagnosis (Citron M. (2004), Strategies for disease modification in Alzheimer's disease, Nat Rev Neurosci 5 (9): 677-85). The large number of people suffering from this disease and requiring constant care and other services will severely affect medical, monetary, and human resources (Suh Y H and Checler F. (2002).) Amyloid precursor protein, presenilins, and alpha-15 synuclein: molecular pathogenesis And pharmacological applications in Alzheimer's disease, Pharmacol Rev. 54 (3): 469-525). Amyloid precursor protein, presenilins, and alpha-15 synuclein: molecular pathogenesis and pharmacological applications in Alzheimer's disease. Pharmacol Rev. 54 (3): 469-525) Thus, it is a growing medical concern.

Cerebral ischemia is one of the leading causes of death and the first one of disability in adults in many countries (Mukherjee, D., Patil, C G, 2011. Epidemiology and the global burden of stroke, World Neurosurg. 76, S85-S90) Currently only tissue plasminogen activator is the drug that is approved for use in human therapy during the acute phase of cerebral ischemia (Howells, D W, Donnan, G A, 2010.) Comes from? PLoS Med. 7, e1000224). Despite the preclinical hopeful results obtained, none of the candidates evaluated has shown consistent clinical improvements. This may be due to the multiplicity of mechanisms involved in the cascade of neuronal damage after cerebral ischemia, which contrasts with the more simplistic view of the proposed neuroprotectors (Minnerup, J., Schäbitz, W R., 2009. Multifunctional actions of approved and Candidate stroke drugs, Neurotherapeutics 6, 43-52). Accumulated preclinical evidence indicates that a highly selective ligand for a given biological target does not always result in a clinically effective drug, particularly in those pathologies involving multiple factors, such as cerebral ischemia. Therefore, drugs acting at a single site in the ischemic cascade, such as $Ca^{2+}$ blockers, glutamate antagonists, GABA agonists, antioxidants/free radical scavengers, phospholipid precursors, and anti-inflammatory agents Have generally failed to be clinically effective (Ginsberg, M D, 2008. Neuroprotection for ischemic stroke: past, present and future, Neuropharmacology 55, 363-389).

Emergent neuroprotective approaches have begun to consider mitochondrial bioenergetic dysfunction. There is evidence to suggest that mitochondria play a key role in ischemic neuronal damage by the activation of noxious signals either by structural and functional damage or by amplification of the cascade, which eventually leads to cell death (Christophe, M., Nicolas, S., 2006. Mitochondria: a target for neuroprotective interventions in cerebral ischemia-reperfusion. Curr. Pharm. Des. 12, 739-757) (Mazzeo, A T, Beat, A., Singh, A., Bullock, M R, 2009. The role of mitochondrial transition pore and its modulation intraumatic brain injury and delayed neurodegeneration after TBI. Exp. Neurol. 218, 363-370) (Perez-Pinzon, M A, Stetler, R A, Fiskum, G., Mitochondrial targets for neuroprotection, J. Cereb. BloodFlow. Metab, 32, 1362-1376). Therefore, there is a growing interest in the identification of new classes of compounds that act simultaneously on certain toxic processes in ischemic neurons, including those acting at the mitochondrial level.

Phenolic or polyphenolic derivatives have been widely reported in the literature to be used in the treatment of diseases of the central nervous system, however, their high water solubility (mainly given by hydroxyl groups), make these compounds have difficulty crossing the blood brain barrier and access the brain. The inventors have obtained the product (5-[(3,4-dihydroxyphenyl) methylidene]-2,2-dimethyl-1,3-dioxane-4,6-dione) or KM 34:

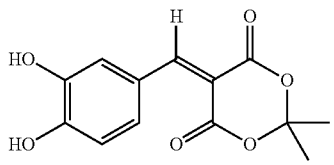 [SMILES: CC1(C)OC(=O)C(=Cc2ccc(O)c(O)c2)C(=O)O1]

Meldrum (2,2-dimethyl-1,3-dioxane-4,6-dione) acid and its derivatives have been used intensively as starting materials for the synthesis of many heterocycles, in particular to evaluate their potential biological activity.

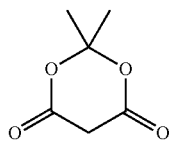

The condensation of Meldrum acid with aromatic aldehydes has been developed in an ethanol-water solution with the presence of catalyst by a highly efficient photochemical process with the environment (A novel light induced Knoevenagel condensation of Meldrum's acid with aromatic aldehydes in aqueous ethanol. Somnath Ghosh, Jhantu Das, Subhagata Chattopadhyay, Tetrahedron Letters, Volume 52, Issue 22, 1 Jun. 2011, Pages 2869-2872).

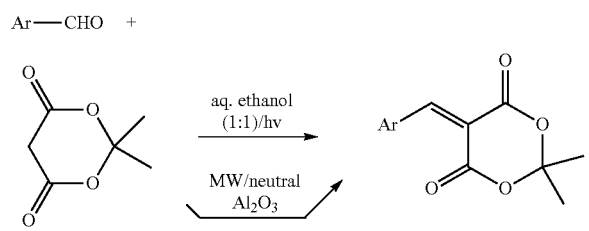

These derivatives show antimicrobial activity. Another series of arylidene analogs of Meldrum's acid (Sandhu H S and all (2010) Synthesis and biological evaluation of arylidene analogues of Meldrum's acid as a new class of antimalarial and antioxidant agents Bioorg Med Chem. 2010 Aug. 1; 18 (15): 5626-33) were evaluated in vitro showing antimalarial and antioxidant activities, as well as inhibitors of platelet aggregation (Abdelaziz El Maatougui, JhonnyAzuaje, Alberto Coelho, Ernesto Cano, Matilde Yanez, Carmen Lopez, Vicente Yaziji, Carlos Carbajales and Eddy Sotelo (4)) Discovery and Preliminary SAR of 5-Arylidene-2,2-Dimethyl-1,3-Dioxane-4,6-Diones as Platelet Aggregation Inhibitors Pages 551-554 (4))

Several patents protect this type of compounds, as well as their use with therapeutic properties. The patent ES2074770 shows the procedure for the preparation of 1,3-dioxane-4,6-dione derivatives.

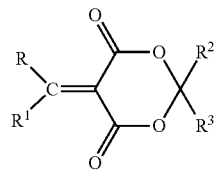

Co-inhibitors of acyl-CoA: cholesterol-acyl transferase, based on N,N',N'-trisubstituted 5-bis-aminomethylene-1,3-dioxane-4,6-dione, are also shown in the patent ES2077985 with the formula:

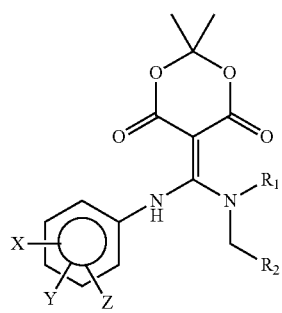

BRIEF DESCRIPTION OF THE DRAWINGS

FIG. 1. Percentage reduction of DPPH (100 μM) by KM-34 (5-400 μM) was determined by changing in the absorbance at 550 nm from a target containing only DPPH and vehicle (zero concentration of KM −34 or AA), after 30 minutes of reaction. Values are expressed as the mean ± SD (n=3). *P<0.05 with respect to the vehicle.

FIG. 2. Activity of KM-34 (5-100 μM) as radical scavenger O2.− expressed as the percentage inhibition of autoxidation of pyrogallol. The same was obtained by varying the absorbance at 420 nm for 1 minute with respect to a blank uninhibited reaction: without KM-34; the slope was calculated for each concentration of the sample and for the target with a R2>0.98. The reaction takes place in 50 μM Tris-HCl pH 8.2 buffer and was initiated by the addition of 0.134 mM Pirogalol*P<0.05 to the carrier (uninhibited reaction).

FIG. 3. Effect of KM-34 (0.1, 1.10, 100 μM) on oxidative damage to 2.8 (A) and 28 mM (B) DR respectively, induced by Fe3+–EDTA and ascorbate. The solutions were incubated 30 minutes at 37° C and contained 10 mM phosphate buffer pH 7.4, 100 µM EDTA, 25 µM FeCl3, DR (2.8 or 28 mM). Reactions were initiated with 100 µM AA. The results are expressed as the percent inhibition of DR degradation relative to a control containing only absolute ethanol: obtained by changes in absorbance at 532 nm. The bars show the mean ± SD (n=3). *P<0.05 with respect to control.

FIG. 4. Maximum absorption data on UV-VIS (200-500 nm) of the 100 µM KM-34 in a mixture of 10 mM phosphate buffer (KH2PO4/ KOH) pH 7.4 and absolute ethanol 14:1 (v:v) and The absorbance in the presence of FeCl2 (50, 100 and 200 µM) dissolved in 10mM HCL.

FIG. 5. Effects of KM-34 (0.01-100 µM) on spontaneous lipid peroxidation and e induced by 100 mM FeCl3 and 100 mM AA. The control contains absolute ethanol instead of KM-34. The samples were incubated at 37° C for 1 hour and then the MDA levels were quantified by thiobarbituric acid (ATB) and the absorbance was determined at 532 nm. Values are expressed as the mean ± SD (n=3). *P<0.05 with respect to the control.

FIG. 6. Cytoprotective effect of KM-34 10001-10 HM) against damage induced by L-glutamate (50 mmol/L) in cultures of PC12 cells. Viability (% live cells) was determined by the MTT assay. Cells were seeded at a density of 5×105 cells/mL in a 96-well plate. KM-34 was added simultaneously to the addition of L-glutamate. The culture was then allowed to incubate at 37° C, 95% O 2 and 5% CO 2 for 4 hours. After this time the supernatant was removed and the cells were incubated with 20 µg of MTT for an additional 2 hours and the absorbance at 450 nm was measured with reference to 630 nm. The results are expressed as percentage of live cells relative to the control (cells without damage, 100% of live cells. * Represents significant differences (p<0.05) with respect to the L-glutamate control.

FIG. 7. Cytoprotective effect of KM-34 (1-100 µM) against damage induced by H2O2 (150 µM) in cultures of PC12 cells. Viability (% live cells) was determined by the MTT assay. Cells were seeded at a density of 5×105 cells/mL in a 96-well plate. The KM-34 was added simultaneously to the addition of the H2O2 mixture. The culture was then allowed to incubate at 37° C, 95% O 2 and 5% CO 2 for 4 hours. After this time the supernatant was removed and the cells were incubated with 20 µg of MTT for an additional 2 hours and the absorbance at 450 nm was measured with reference to 630 nm. The results are expressed as percentage of live cells relative to the control (undamaged cells, 100% live cells). The * represents significant differences (p<0.05) with respect to the H2O2 control.

FIG. 8. Cytoprotective effect of KM-34 (0.001-10 µM) against damage induced by FeSO4 (5 mmol/L) and ascorbic acid (AA, 2 mmol/L) in cultures of PC12 cells. Viability 1% live cells) was determined by the MTT assay. Cells were seeded at a density of 5×105 cells/mL in a 96-well plate. The KM-34 was added simultaneously to the addition of the mixture of FeSO 4 and AA. The culture was then allowed to incubate at 37° C, 95% O 2 and 5% CO 2 for 4 hours. After this time the supernatant was removed and the cells were incubated with 20 µg of MTT for a further 2 hours and the absorbance at 450 nm was measured with reference to 630 nm. The results are expressed as percentage of live cells relative to the control (undamaged cells, 100% live cells. *Represents significant differences (p<0.05) with respect to FeSO4/AA control.

FIG. 9. Effect of KM-34 on damaged animals with 6-OHDA, cylinder test. The graph shows the different treatment groups, evaluated 7 days after the damage. In this case, the neuroprotective capacity of the doses of 2mg and 1mg in the Parkinson's model was observed, as there were statistically significant differences with respect to the animals without treatment. Not being so for the dose of 0.5mg, when not presenting statistically significant differences with respect to the damaged animals without treatment. The values represent the mean percentage of asymmetry, relative to the control group damaged ± SD. Data were analyzed using statistical methods ANOVA and Tukey's *p<0.05.

FIG. 10. Effect of KM-34 on animals damaged with 6-OHDA, exploratory behavior. The graph shows the different treatment groups, evaluated 7 days after the damage. Here the vertical scan values of the different treatment groups are shown. The damaged group has a significantly lower vertical scan than the vehicle control (healthy animals). As the doses of KM-34 are increased, a tendency to increase vertical exploration is observed, being for the group treated with the highest dose statistically significant with respect to the damaging control. The values represent the mean percentage of asymmetry, relative to the control group damaged ± SD. Data were analyzed using statistical methods ANOVA and Tukey's *p<0.05. The results indicate a potential neuroprotective effect of KM34 in Parkinson's disease.

FIG. 11. Effect of KM-34 on spatial memory. In the T labyrinth, KM-34 (2, 4 and 8 mg/k, p.o) was given 1 hour prior to scopolamine (1 mg/kg, i.p.). Data are expressed as mean ± SD (n=7, per group) of the percentage of spontaneous alternation. For statistical anal sis ANOVA and Tukey's multiple comparison test were performed. Different letters differ from each other for p<0.01.

FIG. 12. Effect of KM-34 on the recognition memory of new objects. In the new-object recognition test, KM-34 (2, 4 and 8 mg/kg, p.o) was administered 1 hour prior to scopolamine (1 mg/kg, i.p.) prior to the training phase. The results are expressed as the discrimination rate of the total time by scanning the object N with respect to F. The data are expressed as mean ± SD (n=8, per group). For statistical analysis, ANOVA and Tukey's multiple comparison test were performed. Different letters differ from each other for p<0.01.

FIG. 13. Acute treatment with KM-34 reduced the volume of infarction edema and deficit in rat behavior after 90 min of middle cerebral artery occlusion (MACA) and 23 hours of reperfusion. The different doses of the compound were administered orally 1 hour after reperfusion. (A) Representative brain coronal sections (2 mm thick) of the sham and ischemic groups treated with vehicle or KM-34 (0.1, 0.5 or 1 mg/kg) and stained with 2,3,5-triphenyltetrazolium (TTC) 2%. The red regions correspond to undamaged tissue and white to ischemic regions. (B) Quantitative analysis of cortical, subcortical and total lesion size. (C) Neurological deficit. The bars represent the mean ± SEM (n=8). Different letters in (A) and * in (B): p<0.05, by ANOVA and post hoc of Newman-Keuls. Scale=10 mm.

FIG. 16. Effect of JM-20, KM-34 and its combination on thermocoagulation-induced asymmetry of cortical arteries.

SUMMARY OF THE INVENTION

Figure 14:
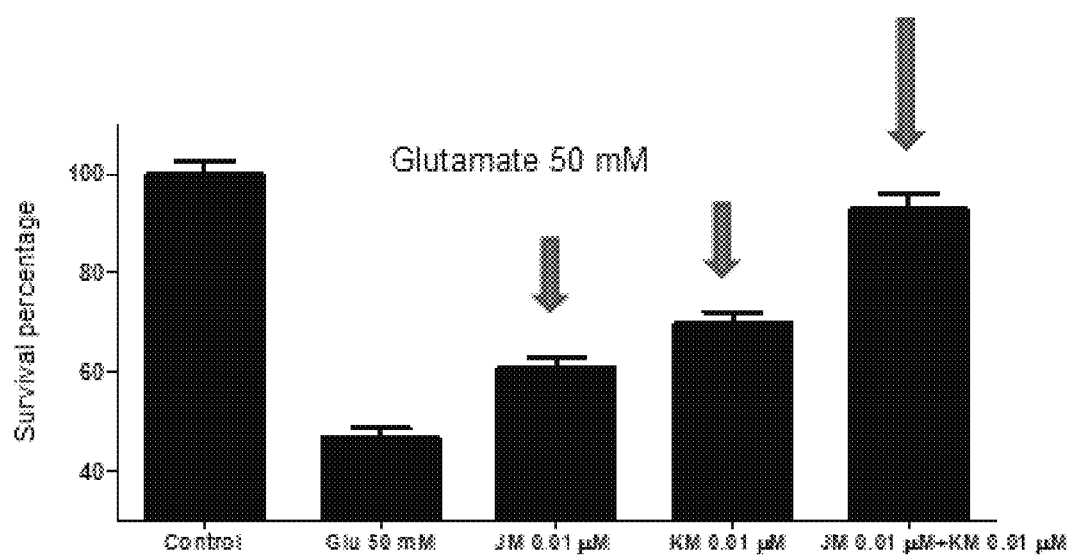
FIG. 14. The survival rate for rats administered 50 mM Glutamate is shown. The control group was not administered 50 mM Glutamate. The remaining four groups were administered 50 mM Glutamate. The "Glu 50 mM" group was not administered any compounds of the invention. The "JM 0.01 µM" group was administered 0.01 µM JM-20. The "KM 0.01 µM" group was administered 0.01 µM KM-34. The "JM 0.01 µM+KM 0.01 µM" group was administered 0.01 µM JM-20 and 0.01 µM KM-34.
Figure 15:
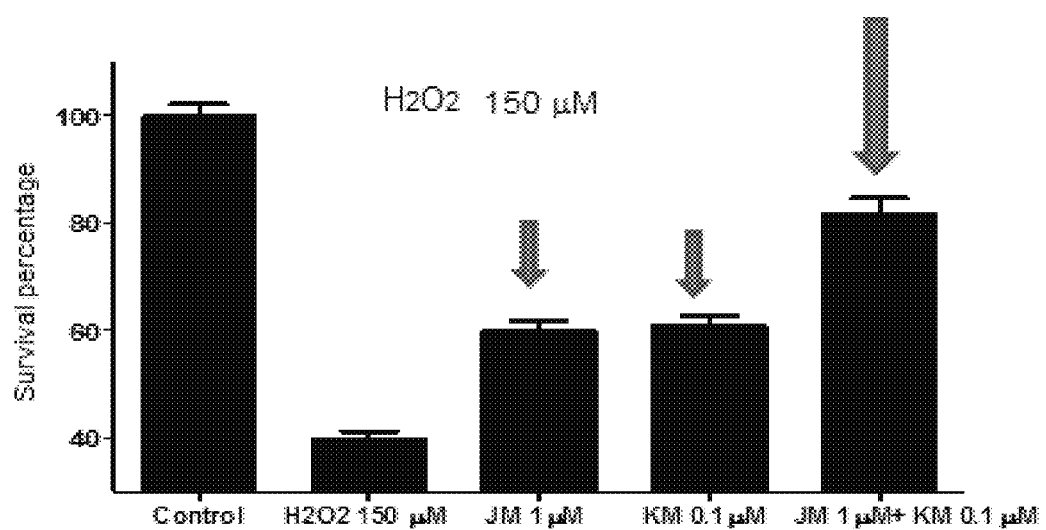
FIG. 15. The survival rate for rats administered 150 µM $H_2O_2$ is shown. The control group was not administered 150 µM $H_2O_2$. The remaining four groups were administered 150 μM $H_2O_2$. The "$H_2O_2$ 150 μM" group was not administered any compounds of the invention. The "JM 1 μM" group was administered 1 μM JM-20. The "KM 0.1 μM" group was administered 0.1 μM KM-34. The "JM 1 μM+KM 0.1 μM" group was administered 1 μM JM-20 and 0.1 μM KM-34.

This invention relates to chemical compounds which exhibit an inhibitory power over Coenzyme A: Cholesterol Acyltransferase (ACAT). Compounds of this type help to reduce the absorption of cholesterol and therefore have an effect on atherosclerosis.

JPH11180975 discloses the compound of formula III, 2,2-dimethyl-5-(4-methoxycarbonylmethyloxyphenylamin-omethylene)-1,3-dioxane-4,6-dione, which has an excellent ultraviolet absorption capacity, properties on the cracking of the skin and low percutaneous absorption capacity.

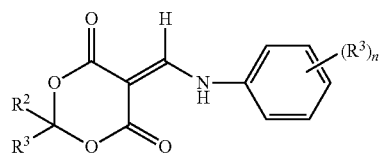

III

U.S. Pat. No. 5,217,174 protects 5-[(3,5-di-tert-butyl-4-hydroxy-phenylamino)-(methyl-pyridin-4-ylamino)-methylene]-2,2-dimethyl-[3]dioxan-4,6-dione.

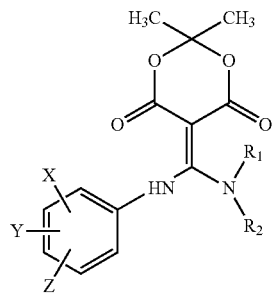

In WO200586661 a compound, a pharmaceutical composition and the method of use for the treatment of metabolic disorders are protected. In this case it is proposed to obtain a product which shows marked activity for the treatment of type II diabetes, in which process the intermediate of general formula:

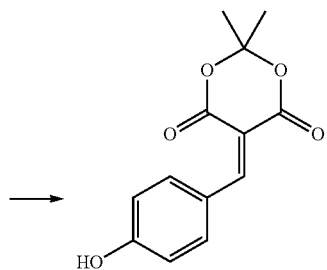

There is a patent in the literature which relates to tricyclic benzodiazepine-type systems fused to 1,4-dihydropyridine derivatives with action on the Central and Vascular Nervous System (CU2009/000172), but this invention does not comprise the combination of such tricyclic derivatives with phenolic or polyphenolic derivatives, which would allow to combine GABAergic, antiglutamatergic, calcium channel modulating, mitoprotective, antioxidant (free radical scavenger and iron chelating), anti-inflammatory and antiapoptotic actions; which would support its use in the treatment of cardiovascular, cerebrovascular, neurodegenerative, neuropsychiatric and neurological diseases, as well as the use of smaller doses and, therefore, of lower collateral effects.

As a further aspect of the present invention, the phenolic compound KM34 in free form or in the form of its salts, hydrates, crystalline forms, metabolites, prodrugs: as well as the combination thereof with a tricyclic benzodiazepine type fused to a 1, 4-dihydropyridine: JM-20 (3-ethoxycarbonyl-2-methyl-4-(2-nitrophenyl)-4,11-dihydro-1H-pyrido[2,3-b][1,5]benzodiazepine), may function as the active ingredient (s) of different formulations.

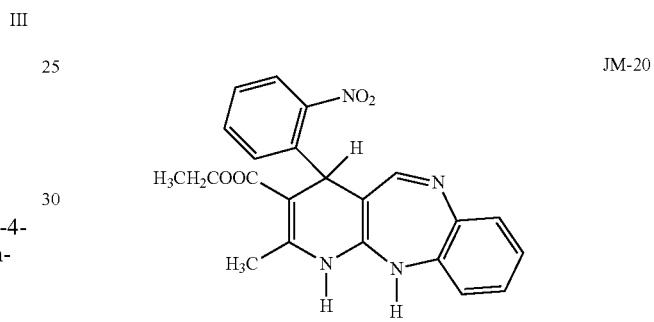

JM-20

The active ingredient(s) may be administered in admixture with at least one non-toxic chemically inert adjuvant, diluent and/or carrier, hereinafter recognized as excipients, included in the pharmaceutical compositions proposed.

The pharmaceutical compositions contemplating any liquid composition, solid or semi-solid, can be administered orally, bucopharyngeal, sublingual, parenteral eg intramuscular, intravenous, intradermal or subcutaneous, topical, transdermal, tracheal, bronchial, nasal, pulmonary, rectal or other routes of administration.

The disclosed pharmaceutical compositions will comprise the suitable excipients for each formulation. The formulations are prepared in a conventional manner by methods collected in the state of the art. The excipients are selected according to the pharmaceutical form of choice according to the route of administration.

DETAILED DESCRIPTION OF THE INVENTION

The active ingredient(s) for administration to humans may be contained in pharmaceutically acceptable dosage forms, including, but not limited to, such presentation forms: tablets (including sublingual, coated and chewable tablets), hard and soft capsules (including Microcapsules, nanoparticles and pellets), solutions (oral drops, syrups), parenteral solutions, transdermal patches, implants and other retard systems, ointments (creams and gels), nasal spray, mucoadhesives, suppositories, suspensions, reconstitution or addition powders In foods, among other dosage forms encompassed by this invention.

By employing technological processes known in the state of the art, the active ingredient(s) can be formulated into dosage forms suitable for administration by mixing them with excipients such as liquid, solid or semi-solid auxiliary substances, organic and inorganic compounds, Of natural or synthetic origin. These include: filler solids, diluents, binders, solvents, emulsifiers, lubricants, disintegrants, glidants, colorants, pigments, polymers, sweeteners, plasticizers, absorption enhancers, penetration enhancers, surfactants, cosurfactants, specialized oils and/or buffer systems, which provide the active compounds or their physiologically acceptable salts with physical, chemical and/or biological stability.

Some excipients used in the formulation of dosage forms containing the active substance(s), other than the use of other auxiliary substances, are: starches, lactose, cellulose and its derivatives, sucrose, sorbitol, mannitol and other sugars, talc, dioxide Polyvinylpyrrolidone, polyvinylpyrrolidone, povidones, gelatine, lacto-proteins, citrates, tartrates, alginates, dextran, ethylcellulose, cyclodextrins, silicone elastomers, polysorbates, amylopectin, parabens, animal and vegetable oils, propylene glycol, sterile water, mono or polyhydric alcohols such as glycerol, magnesium stearate, calcium stearate, sodium stearyl fumarate, sodium lauryl sulfate, glycerine and polyethylene glycol waxes, among others.

Solid oral dosage forms, such as tablets, microgranules, nanoparticles, pellets, reconstitution powders or capsules, containing the active ingredient(s) according to the present invention may be immediate release or modified release.

A pharmaceutical form of choice according to the present invention are the tablets, containing as the active pharmaceutical ingredient the active ingredient(s), a mixture is prepared with microcrystalline cellulose, corn starch, crospovidone, a solution of polyvinylpyrrolidone and Sodium to form a granulate, this is dried to complete process in fluidized bed and mixed with magnesium stearate and talc, the tablets are subsequently made using a system of rotary punches for their manufacture, finally the tablets are coated with a suspension of hydroxypropylmethylcellulose, Polyethylene glycol 4000, titanium dioxide and colorant.

By coating the tablets elegance is achieved in the finished form and unpleasant taste is avoided, this is achieved with a flavor masking agent, such as a copolymer of methyl acrylic acid, ethylcelluloses, methylhydroxypropylcellulose or other polymers. The tablets can be obtained either by the above-described wet granulation method or by the direct compression method using excipients for direct compression and decreasing steps in the tabletting step provided that it is operated at low doses.

The tablets may be modified release and may contain the active ingredient(s) in microgranules, nanoparticles or matrix systems, using excipients such as: polyethylene oxide, hydroxypropylmethylcellulose 2910, magnesium stearate, sodium chloride, red ferric oxide, cellulose acetate, polyethylene glycol 3350 and opadry.

The pharmaceutical compositions according to the present invention may contain pharmaceutically acceptable, permeable, biodegradable and water-insoluble polymers to control their release profile, whereby modified (immediate, delayed or controlled) release dosage forms may be obtained. These polymers may be used in the coating of tablets, microgranules, capsules, in the preparation of nanoparticles, as release matrices in pellets, tablets, granules or in admixture with the other excipients included in any other dosage form mentioned in the present invention.

For oral administration, other suitable pharmaceutical compositions are hard capsules, soft capsules and pharmaceutical powders, the physiologically acceptable active ingredient(s) may be dosed in the form of hard gelatin or cellulose capsules, for example, containing a mixture of the Active pharmaceutical ingredient with excipients commonly used in solid forms as described for tablets, said blend may be obtained by dry, wet granulation, extrusion, pelletisation, microencapsulation, or dosing microtabs. Dosing in soft gelatine capsules will employ conventional methods of preparation and may be prepared by mixing the active ingredient(s) with vegetable oils, fats or other similar vehicles suitable for formulation.

In the case of pharmaceutical powders these may be made by simple mixing of the physiologically acceptable active ingredients with fillers, suspending agents, sweeteners, flavorings and preservatives. Although the spray drying methodology at an inlet temperature between 100° C. and 150° C. and an outlet temperature between 50° C. and 90° C. were employed in the preparation of the powders in the present invention using excipients such as Dextran, polyethylene glycol 4000 and sodium lauryl sulfate, among others, to improve the solubility of the active pharmaceutical ingredient as a function of its proper incorporation into the body in solutions, or by adding it to foods as juices.

For rectal administration, the physiologically acceptable active ingredient(s) may be dosed in the form of suppositories, foams or rectal solution in microenemas, which may contain a mixture of the active compounds with a solid neutral fat base (Witepsol 45) or another A similar carrier suitable for formulation may also be used sorbitan monooleate, polysorbate 20, emulsifying wax, anhydrous colloidal silica, sodium metabisulfite, disodium edetate, methyl parahydroxybenzoate, sodium phosphates, macrogol 300, glycerol, water, propane, isobutane and n-butane.

For oral liquid administration, the physiologically acceptable active ingredient(s) may be formulated as syrups, elixirs, concentrated droplets or suspensions, having a pharmaceutically acceptable carrier as a mixture of ethanol, water, glycerol, propylene glycol and/or polyethylene glycol, Among others, carboxymethylcellulose or other thickening agents, may contain colorants, flavorings, sweeteners (sucralose, aspartame, cyclamate, stevia), preservatives (parabens, benzoates). These liquid dosage forms may be prepared from the reconstitution of powdered pharmaceutical compositions with a suitable solvent prior to use.

For parenteral administration, the physiologically acceptable active ingredient(s) may be formulated as injectable solutions. Such solutions may contain stabilizing ingredients, preservatives and/or buffer ingredients. In the present invention the active pharmaceutical ingredient is in a solution of 96% ethanol, benzyl alcohol, propylene glycol, benzoic acid, sodium benzoate, sodium hydroxide, water for injection, other excipients such as polyethylene glycol 400, sodium citrate And citric acid. Solutions for parenteral administration containing the physiologically acceptable active ingredient(s) may also be prepared by reconstituting a dry (lyophilized) pharmaceutical composition with a suitable solvent prior to use comprising the use of auxiliary substances such as mannitol, polysorbate 80, Sodium chloride, among others.

For the subdermal administration, the physiologically acceptable active ingredient(s) may be dosed in the form of implants using elastomeric auxiliaries of silicone and anhydrous colloidal silica, although other polymers of pharmaceutical use may be used for the preparation of the pellet.

For transdermal administration, the physiologically acceptable active ingredient(s) may be formulated as patches, in which case the active pharmaceutical ingredient is contained in a carrier consisting of a solution of acrylic copolymer, ethanol, light liquid paraffin, palmitate Of isopropyl, polyethylene terephthalate, ethylene vinyl acetate and a silicone layer on the inside of the release sheet (with a nominal release rate of 15 mg/day, on a surface of 12.75 cm 2).

EXAMPLES

Example 1. Synthesis of 5-(3,4-Dihydroxy-benzylidene)-2,2-dimethyl-1,3-dioxan-4,6-dione Equimolar amounts of 3,4-dihydroxybenzaldehyde and Meldrum's acid are mixed in a balloon equipped with magnetic stirring using deionized water as the solvent in the proportion of 1-2 L per mole of reactants. The reaction mixture is stirred for about 3-5 hours. After this time a yellow precipitate is obtained which is collected by vacuum filtration, washed three to five times with water and placed in a desiccator. The reaction is monitored by thin layer chromatography (silica gel) using n-hexane-ethyl acetate (1:1) as the mobile phase.

Reaction time (3-5 h); Yield>75%

Melting temperature: 154-157° C. (uncorrected).

PREPARATION OF THE DIFFERENT FORMULATIONS (from phenolic or polyphenolic compound derivatives and from derivatives of phenolic or polyphenolic compounds combined with tricyclic benzodiazepine-like systems fused to derivatives of 1,4-dihydropyridines) FOR BIOLOGICAL EVALUATIONS.

Example 2. Preparation of a Suspension Powder Formulation Containing the KM 34 as the Active Pharmaceutical Ingredient Each teaspoon (5 mL) of KM 34 powder for suspension contains:

| COMPONENT | QUANTITY | FUNCTION |
|---|---|---|
| KM 34 | 40.00 mg | Active ingredient |
| Polyvinylpyrrolidone (Kollidon K-30) | 50.00 mg | Suspension agent |
| Crospovidone (Kollidon CL-M) | 133.33 mg | Suspension agent |
| Magnesium oxide heavy | 210.00 mg | Flavor masking agent |
| Saccharin Sodium | 16.66 mg | Sweetener |
| Mint Flavor Powder | 13.33 mg | Flavoring Agent |
| Strawberry Flavor Powder | 20.00 mg | Flavoring Agent |
| Sucrose | 1183.34 mg | Filler |

Brief Description of the Technological Process:

Sodium Saccharin and Saccharose by high speed mill and sieve by mesh #20 Active Ingredient, Mint Taste Powder and Magnesium Oxide Heavy and by mesh #60 Strawberry Taste Powder.

Weigh the quantities of raw materials according to the formulation described.

Mix for 10 minutes in the Vanguard V-5 mixer.

Collect mixed product in tanks with double nylon bag.

Transfer the product to the Filler—Tap and pack 5 grams of the product in 60 mL amber bottles.

Example 3. Preparation of a Tablet Formulation Containing the KM 34 as Active Pharmaceutical Ingredient Each 120.00 mg tablet contains:

| Component | Quantity | Function |
|---|---|---|
| KM 34 | 40.00 mg | Active ingredient |
| Corn starch | 23.00 mg | Disintegrant |
| Polyvinylpyrrolidone K-25 | 4.00 mg | Binder |
| Lactose monohydrate | 50.50 mg | Filling |
| Magnesium Stearate | 1.50 mg | Lubricant |
| Colloidal Silicon Dioxide | 1.00 mg | Lubricant |
| Ethanol, Class C * | 12.00 µl | Solvent |
| Deionized water * | 12.00 µl | Solvent |

* They evaporate during the drying process.

Brief Description of the Technological Process:

1. Sieve active ingredient, starch and lactose per 20 mesh.
2. Weigh all components of the formulation according to the amounts stated in the formula.
3. To prepare the binder solution, pour the mixture of water and ethyl alcohol Class C into a saucepan with a T-shirt of steam, add the polyvinylpyrrolidone and stir until completely dissolved.
4. Charge the mixer with the active ingredient, starch and lactose (internal phase components). Mix for 15 min.
5. Add the binder solution slowly using the peristaltic pump, complete the required degree of wetting using water and ethyl alcohol class C (1:1) if necessary. Granule by mill at low speed.
6. Dry the granulate in a fluidized bed. At 10 min take a representative sample of the granulate, degranule and check the residual moisture thereof; The value of said moisture should be between 0.8 and 1.2%.
7. Mix dry granules with lubricants for 10 min.
8. Compress in a high-speed rotary machine using flat, bevelled and grooved dies of ¼" (¼ PBR), adjusting the die cutter to obtain tablets with the following parameters:

Mass: 120.0 mg±10%

Height: 2.6±0.10 mm

Hardness: 4.0±1 KgF

Friability: less than 1%

Example 4. Preparation of a Formulation in Injectable Form Containing the KM 34 as Active Pharmaceutical Ingredient Each KM 34 bulb (2 mL) contains:

| Component | Each mL contains | Amount Per Unit of Dose | Function |
|---|---|---|---|
| KM 34 | 5.0 mg | 10.0 mg | Active ingredient |
| Cremofor ELP | 527.0 mg | 1054.0 mg | Coadjuvant |
| Hydrochloric acid 1N c.s.p | — | — | Sln pH adjustment |
| Dehydrated Alcohol c.s. | 1.0 ml | 2.0 mL | Solvent |
| *Nitrogen cs | — | — | |

1. Verify that the reactor is completely dry after sterilization, otherwise rinse it with dehydrated alcohol.
2. Prepare a 1 N hydrochloric acid solution for pH adjustment.

3. Add a portion of Cremofor ELP and dehydrated alcohol to the reactor. Mix at 420 rpm.
4. Weigh the active ingredient and add portions of dehydrated alcohol to the beaker containing it, dispense it with the glass stirrer and add it to the reactor, repeat this operation until the whole active ingredient is drawn and the dehydrated alcohol is exhausted.
5. In the reactor keep stirring for 60 min. At 420 rpm until total dissolution of the active ingredient is achieved.
6. Add the rest of Cremofor ELP by dragging the remainder with dehydrated alcohol, shaking for 10 min. At 420 rpm.
7. Determine the pH of the solution and adjust with 1N hydrochloric acid solution between 5.0-6.0.
8. Complete the volume of the solution by adding dehydrated alcohol. Stir for 5 minutes at 420 rpm.
9. Take 10 mL of the solution and send it to the laboratory for process control (titration and pH)
10. Verify proper assembly of the filling and nitrogenation systems.
11. Perform the integrity test of the Sartobran P MidiCaps filter, (0.45+0.2 μm) porosity with dehydrated alcohol.
12. After the process control is finished, pressurize the reactor using nitrogen (0.7-1.0 bar) to drive the solution through the Sartobran P cartridge filter of 0.45 μm+0.2 μm porosity. Fill and seal the bulbs by measuring 2.2 mL of the solution.

Example 5. Preparation of a Tablet Formulation Containing the Combination of KM 34 and JM 20 as the Active Pharmaceutical Ingredient Each 120.00 mg tablet contains:

| Component | Quantity | Function |
| --- | --- | --- |
| KM 34 | 20.00 mg | Active ingredient |
| JM 20 | 20.00 mg | Active ingredient |
| Corn starch | 23.00 mg | Disintegrant |
| Polyvinylpyrrolidone K-25 | 4.00 mg | Binder |
| Lactose monohydrate | 50.50 mg | Filling |
| Magnesium Stearate | 1.50 mg | Lubricant |
| Colloidal Silicon Dioxide | 1.00 mg | Lubricant |
| Ethanol, Class C * | 12.00 μl | Solvent |
| Deionized water * | 12.00 μl | Solvent |

* They evaporate during the drying process.

Brief Description of the Technological Process:
1. Sieve active ingredients, starch and lactose per mesh 20.
2. Weigh all components of the formulation according to the amounts stated in the formula.
3. To prepare the binder solution, pour the mixture of water and ethyl alcohol Class C into a saucepan with a T-shirt of steam, add the polyvinylpyrrolidone and stir until completely dissolved.
4. Charge the mixer with the active ingredient, starch and lactose (internal phase components). Mix for 15 min.
5. Add the binder solution slowly using the peristaltic pump, complete the required degree of wetting using water and ethyl alcohol class C (1:1) if necessary. Granule by mill at low speed.
6. Dry the granulate in a fluidized bed. At 10 min take a representative sample of the granulate, degranule and check the residual moisture thereof; The value of said moisture should be between 0.8 and 1.2%.
7. Mix dry granules with lubricants for 10 min.
8. Compress in a high speed rotary machine using flat, bevelled and slotted dies of ¼" (¼ PBR), adjusting the die cutter to obtain tablets with the following parameters:
Mass: 120.0 mg±10%
Height: 2.6±0.10 mm
Hardness: 4.0±1 KgF
Friability: less than 1%

Example 6. Preparation of a Formulation in the Form of Oral Drops Containing the Combination of KM 34 and JM 20 as Active Pharmaceutical Ingredient Each mL (20 drops) contains:

| Component | Quantity | Function |
| --- | --- | --- |
| KM 34 | 20.0 mg | Active ingredient |
| JM 20 | 20.0 mg | Active ingredient |
| Propylene glycol | 300.0 mg | Co-adjuvant solvent |
| Kollidon 25 | 160.0 mg | Viscous Agent |
| Saccharin Sodium | 12.5 mg | Sweetener |
| Red ponceaux | 0.05 mg | Coloring |
| Citric acid | 5.535 mg | pH stabilizer |
| Sodium Citrate Dihydrate | 20.0 mg | pH Stabilizer |
| Ethyl alcohol | 100.0 mg | Co-adjuvant solvent |
| Methylparaben | 1.8 mg | Antimicrobial preservative |
| Propylparaben | 0.2 mg | Antimicrobial preservative |
| Strawberry flavor liquid (soluble) | 20.0 mg | Flavoring |
| Purified water q.s. | 1.0 mL | Vehicle |

Brief Description of the Technological Process:
1. Measure the pH and conductivity of the purified water at the time of manufacturing the product.
2. Pour the propylene glycol into the reactor.
3. In an appropriate stainless steel auxiliary vessel, dissolve saccharin sodium in purified water.
4. Incorporate the Kollidon 25, sprinkle it gradually, and stir for a time not less than 30 minutes until total dispersion.
5. Stir and apply heat to the preparation, keeping the temperature between 40-50° C., for 30 minutes.
6. Incorporate the active ingredients to the resultant from the previous step, in small portions, keeping the stirring constant for 30 minutes.
7. Remove the heat and wait for the preparation to take room temperature, 30±2° C.
8. Dissolve methylparaben and propylparaben in the ethyl alcohol "C" class in a suitable auxiliary glass or stainless steel vessel, stirring constantly until complete dissolution.
9. Add in the resultant from the previous step the strawberry flavor liquid soluble and stir until completely homogeneous.
10. Incorporate the resultant from the previous step into the reactor tank, slowly, with strong and constant stirring.
11. In a glass or stainless steel container of suitable capacity, dissolve citric acid and sodium citrate dihydrate in purified water, stirring after each addition until it is completely dissolved.
12. Incorporate the resultant from the previous step into the reactor tank, slowly, with strong and constant stirring.
13. In a glass or stainless steel vessel of suitable capacity, dissolve the red ponceaux in purified water, stirring until completely dissolved and incorporated into the preparation.

14. Make up to the predetermined volume with purified water. Shake to uniform.
15. Check that pH is maintained in the range of 4.0-6.0.
16. Perform the final filtration, check the organoleptic characteristics.
17. Pack the final preparation into the 15 ml amber glass vials with 15.0±1.0 mL of the solution, sealing them properly, using the caps with the dropper reducers for oily product.

Example 7. Preparation of a Formulation in Injectable Form Containing the Combination of KM 34 and JM 20 as Active Pharmaceutical Ingredient Each bulb (2 mL) contains:

| Component | Each mL contains | Amount Per Unit of Dose | Function |
|---|---|---|---|
| KM 34 | 2.5 mg | 5.0 mg | Active ingredient |
| JM 20 | 2.5 mg | 5.0 mg | Active ingredient |
| Cremofor ELP | 527.0 mg | 1054.0 mg | Coadjuvant |
| Hydrochloric acid 1N q.s. | — | — | Solution for pH adjustment |
| Dehydrated Alcohol q.s. | 1.0 ml | 2.0 mL | Solvent |
| Nitrogen qs | — | — | |

1. Verify that the reactor is completely dry after sterilization, otherwise rinse it with dehydrated alcohol.
2. Prepare a 1 N hydrochloric acid solution for pH adjustment.
3. Add a portion of Cremofor ELP and dehydrated alcohol to the reactor. Mix at 420 rpm.
4. Weigh the active ingredients and add portions of dehydrated alcohol to the beaker containing it, disperse it with the glass stirrer and add it to the reactor, repeat this operation until all the active ingredients have been drained and all the dehydrated alcohol is exhausted.
5. In the reactor keep stirring for 60 min. At 420 rpm until achieving total dissolution of the active ingredients.
6. Add the rest of Cremofor ELP by dragging the remainder with dehydrated alcohol, shaking for 10 min. At 420 rpm.
7. Determine the pH of the solution and adjust with 1N hydrochloric acid solution between 5.0-6.0.
8. Complete the volume of the solution by adding dehydrated alcohol. Stir for 5 minutes at 420 rpm.
9. Take 10 mL of the solution and send it to the laboratory for process control (titration and pH)
10. Verify proper assembly of the filling and nitrogenation systems.
11. Perform the integrity test of the Sartobran P MidiCaps filter, (0.45+0.2 μm) porosity with dehydrated alcohol.
12. After the process control is finished, pressurize the reactor using nitrogen (0.7-1.0 bar) to drive the solution through the Sartobran P cartridge filter of 0.45 μm+0.2 μm porosity. Fill and seal the bulbs by measuring 2.2 mL of the solution.

Biological Activity Realization Tests

Example 8. Antioxidant Activity of KM-34

KM-34 Capacity to Reduce DPPH Radicals.

One of the most commonly used methods to estimate antioxidant activity is to evaluate the ability of different compounds to reduce DPPH radicals, which can be determined spectrophotometrically (Brand-Williams et al., 1995). DPPH is a stable free radical due to the delocalization of e-available over the entire molecule, demonstrating that the molecules do not dimerize. Electron delocalization causes the intense violet coloration of the DPPH radical form when it is prepared in ethanol solution (Molyneux et al., 2004).

The results of the effect of KM-34 (5-400 μM) on the DPPH radicals are shown in FIG. 1. In the same it can be observed that the % reduction of the radical is directly proportional to the increase of KM concentrations; At concentrations higher than 5 μM and after 30 minutes of reaction % inhibition of the DPPH radical significantly ($p<0.05$) was observed with respect to the vehicle. At concentrations above 50 μM the KM-34 reached its maximum response. The IC 50 value obtained for KM was approximately 2.4 times lower than that obtained for ascorbic acid (AA) used as the reference compound.

Given its aromatic nature, this dihydroxy substituted compound behaves as an excellent electron donor (Vermerris and Nicholson, 2006) by electronic conjugation (Merchan et al., 1981). The lower IC50 value of KM-34 (16.26 μM) than AA (38.70 μM) demonstrates the strong antioxidant power of this molecule. The fact that the presence of phenolic groups confers antioxidant properties (Fraga, 2007), allows to represent the effect of this polyphenol (AH) in the following way:

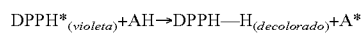

$$DPPH*_{(violeta)} + AH \rightarrow DPPH-H_{(decolorado)} + A*$$

The stability of the radical formed by the action of KM is an essential condition for its antioxidant activity. The negative charge is delocalized in the aromatic system, which causes a marked ion stability (Merchán et al., 1981).

Activity of Radical Scavenging $O_2.^-$ of the KM-34 in the Pyrogallol Test.

A non-enzymatic system generating these radicals was used to evaluate the $O_2.^-$ sequestration activity of KM-34, which catalyzes the autoxidation of pyrogallol, forming a colored compound that absorbs at 420 nm (Marklund, 1985). As shown in FIG. 2, concentrations of KM-34 greater than 5 μM significantly inhibited (for $p<0.05$) the formation of the pyrogalol oxidized form with respect to the vehicle, the IC 50 value was 11.04 μM. From 50 μM, the oxidation of pyrogallol was totally inhibited.

The results of this trial support the fact that KM-34 is a potent radical scavenger O2-, responsible for propagation reactions that accelerate the formation of the pyrogalol oxidized form. Under physiological conditions of overproduction and depletion of its hijackers, O2.— can interact with the sulfhydryl groups of proteins and neighboring enzymes causing their inactivation and initiate a cascade of oxidative events, mainly through the Fenton-Haber-Weiss reaction. It may also mobilize iron from the intracellular ferretine reserves (Brent and Rumack, 1993). This dihydroxyphenol (KM-34) could prevent the damage caused by O2.— and the formation of OH, more reactive.

Protective Effect of KM-34 on Degradation of 2-Deoxy-D-Ribose.

To evaluate the protective action of KM-34 on the oxidative degradation of DR (product of the effect of OH. radicals), the results shown in the graphs (A and B) corresponding to concentrations of DR 2.8 and 28 mM respectively. In both cases the significant results (* $P<0.05$ with respect to the negative control) are observed at concentrations of KM-34 greater than 10 μM.

The process of formation of OH. radicals, as well as the damage caused to DR, occur through the following reactions (Pardo et al., 2006):

(1)

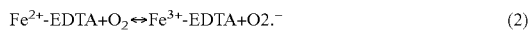
(2)

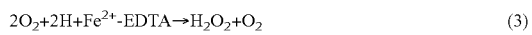
(3)

(4)

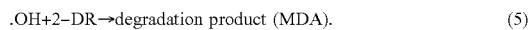
(5)

In this way we can understand the levels where KM-34 could act, which demonstrated inhibition of the formation of the main product of degradation of DR, MDA (monitored spectrophotometrically at 532 nm) at values between 10 and 100 µM independently Of the concentrations of DR used. Although previous studies demonstrated the reduction capacity of KM-34 on radicals DPPH and $O_2.^-$, which could also be expected for the radical .OH, this assay suggests that in those systems where the production of ROS is mediated by iron, (Pardo et al., 2006). However, it is not possible to predict the formation of these species by the coordination of the metal. This compound presents in its structure a catechol group, ketone groups and unsaturations that can contribute to the antioxidant activity by iron binding (Perron and Brumaghim, 2009). The high formation constant of the Fe3+-EDTA complex (logK=25.5) may to some extent prevent the KM-34 from displacing the latter, however, the formation constant for the Fe2+-EDTA complex is approximately half relative to the complex Fe3+-EDTA and may be sufficient to allow KM-34 to stimulate the autoxidation of Fe2+ (Pardo et al., 2006), preventing this metal from participating in Fenton-Haber-Weiss reactions. On the other hand, experimental tests carried out in the LSO demonstrate the interaction of KM-34 with H2O2, resulting in the formation of stable epoxides (unpublished results). This may explain another mode of inhibition of the Fenton reaction by KM-34.

Spectrophotometric Evidence of Interactions Between KM-34 and $Fe^{2+}$.

In order to verify the existence of possible interactions between KM-34 and Fe2+ (through modifications in their spectra), the following results were obtained:

In the experimental results shown by the graph (FIG. 4), it can be seen that the absorbance of the KM-34 at the predetermined absorption maxima 262, 345 and 472 (nm respectively) is modified as the concentration of the ferrous ion increases. This could indicate possible interactions between Fe2+ and KM-34 where the ion is stabilized at Fe3+ by unsaturated ligands due to the stabilization of the larger crystalline field from an electron configuration d6 (Fe2+) to a d5 (Fe3+) (Hider et al., 1981, Hider et al., 1983). This justifies the response obtained in the oxidative degradation test of DR where it was observed that the KM-34 in these conditions seems to act more as a coordinator of Fe2+ than as a .OH scavenger. This result would be very good if we consider that Fe2+ actively participates in processes that give rise to ERO as the reaction of Fenton-Haber-Weiss (Pardo, 2007), if the KM-34 could maintain controlled the ion by its chelation, The risk of ROS formation would be lower.

Effects of KM-34 on Spontaneous or Induced Fe3+/AA POL in Rat Brain Homogenate.

The brain homegenate is rich in phospholipids, which undergo spontaneous or induced autoxidation by the presence of FeCl3 and AA, where the latter is oxidized at the expense of the metal being reduced and thus the ion is available to catalyze the Fenton-Habber reaction-Weiss (Hiroi et al., 2005; Kooncumchoo, 2005). The effects of KM-34 on these processes are shown in FIG. 5. The compound significantly inhibited (p0.05) the spontaneous POL and induced Fe3+/AA mixture at concentrations higher than 0.1 and 10 µM respectively with respect to Uninhibited reaction.

The POL has been recognized, in the last 3 decades, as an event of great importance, both from the physiological and pathophysiological point of view. The increase of the POL is considered as an important and essential cause of the initiation of EO related to the damage to several tissues, cell death and the additional progression of many acute and chronic diseases. MDA referred to high concentrations as toxic and mutagenic and hydroxyalkines (HAL) are terminal products and markers of POL (Leon, 2010). Results previously reported indicate that KM-34 is able to inhibit this spontaneous oxidative process avoiding the formation of MDA at concentrations higher than 0.1 µM. This is indeed what is expected, an aspect that is further reinforced when the potent capacity of this polyphenol to sequester RL as DPPH and O2 has been demonstrated—and leads us to believe that the KM-34 could capture other RL generated during the POL as The lipoperoxyl (LOO.) and alkoxyl (LO.), behaving like a chain-breaking antioxidant. For the case of POL catalyzed by the Fe3+/AA (100 mM) mixture, although the inhibition may appear less marked (from 10 µM KM-34), they are also significant results if one considers that the oxidative process is higher. The AA reduces Fe3+ to Fe2+, a state in which it can participate in the formation of OH radicals through the Fenton-Haber-Weiss chemical reaction. These radicals are able to remove a hydrogen atom from a polyunsaturated fatty acid (LH) and initiate oxidative damage (Hiroi et al., 2005; Kooncumchoo, 2005). The results in this case suggest that in addition to the direct sequestration of RL formed, there could be interaction between KM-34 and iron, thus preventing it from participating in the stages of initiation and propagation of peroxidation, keeping it complex in a Form inactive from the redox point of view.

Protective Effects of KM-34 Against the Action of L-Glutamate.

The excitotoxicity process is defined as the neuronal damage caused by the excessive activation of glutamatergic receptors. The entry of high Ca 2+ levels after activation of the receptors stimulates the activation of enzymes such as Nitric Oxide Synthase (NOS), which generates ERN/ERO at high concentrations leading to cell death (Nakamura and Lipton, 2010; Yang et al. [Links] [Article in Spanish] Torregrosa G, et al., 2009). High levels of glutamate or other excitatory amino acids are involved in the uptake of cysteine (essential for the synthesis of antioxidants such as SOD), which decreases the antioxidant defenses of neurons against oxidative processes (Emerit et al., 2004; Sorg, 2004).

The results obtained in multiple models of excitotoxicity indicate that glutamate significantly inhibits (P<0.01) cell viability, identifying cellular morphological changes (microscopic) in the presence of this NT (Yang et al., 2010). In this sense, FIG. 6 shows the results obtained from the experiment developed with 50 mM L-glutamate to demonstrate the cytoprotective effect of KM-34. This compound at concentrations greater than 0.01 µM and in the presence of L-glutamate, inhibits cell damage significantly (P<0.01) with respect to the negative control. At values above 1 µM KM-34, the cytoprotection response is greater than 80%.

The high production of ERN/ERO is one of the mechanisms that mediates the process of cellular excitoxicity carried out by high concentrations of glutamate (Yang et al., 2010). Previous studies demonstrated the ability of KM-34 to capture RL, the results obtained in this trial being another example of this, where KM-34 could capture ERN/ERO avoiding the damages that these cause during excitotoxicity. Other mechanisms proposed to respond to the high cytoprotective capacity shown by KM-34 and which have been described for other types of polyphenols are the possible activation of antioxidant enzymes as well as the inhibition of NADPH oxidase, which strongly favors the processes Oxidatives (Kovacsova et al., 2010).

Cytoprotective Effect of KM-34 Against Damage Induced by $H_2O_2$.

$H_2O_2$ is formed in vivo spontaneously or enzymatically. At low concentrations this may be poorly reactive, however at high concentrations it may interact with and generate inactivation of the energy generating systems of the cells. In addition $H2O2$ is able to oxidize —SH groups of proteins and cause DNA strand rupture. Their most damaging effect is the formation of catalyzed transition metals by the Fenton-Habber-Weiss reaction (Martinez, 2005). This is based on the use of $H2O2$ in this test, with the aim of observing if the KM-34 is capable of reversing the damages caused by the chemical agent. FIG. 7 shows the results obtained, showing that concentrations of KM-34 higher than 5 μM achieved significant effects of cellular survival, reaching values of response higher than 50% from 25 μM KM-34.

Several experimental results clearly indicate that $H2O2$ is a mediator of multiple physiological events and its excess would lead to multiple pathological conditions (Leon, 2010). This chemical species may be involved in the formation of other ROS, thus increasing its harmful effect, leading to antioxidant compounds such as KM-34 to play a key role in damage control. The results obtained during this test demonstrate this, since at concentrations higher than 5 μM the KM-34 increased the cellular viability of the PC12 exposed to 150 μM of $H2O2$. At concentrations higher than 50 μM, the % cell survival is close to 90.

The uptake of RL may be the fundamental mechanism by which KM-34 exerts its protective effect on this model, once again demonstrating the reduction potential of KM-34 against radical species such as $O_2$. generated from $H2O2$. In view of the interaction between KM-34 and $H2O2$ (result discussed in DR test), the inhibition of the Fenton-Habber-Weiss reaction by KM-34 could be explained, in addition to the damages caused by $H2O2$ by itself.

Protective Effect of KM-34 Against Damage Induced by $FeSO_4$/AA.

The $FeSO_4$/AA system is a strong catalyst for oxidative reactions in cells such as PC12 leading to their death (Hiroi et al., 2005; Núñez et al., 2011). KM-34 in the presence of this pro-oxidant system showed cytoprotective effects at concentrations higher than 0.001 μM. At concentrations greater than 1 μM the % cell survival was greater than 90% (FIG. 8).

These results demonstrate the potent protective capacity of KM-34, which at concentrations between 0.01-10 μM achieves 90 out of 100 cells to survive oxidizing conditions. These results confirm that KM-34 could act by several mechanisms that reinforce its antioxidant properties. These may be RL uptake and iron chelation, already mentioned several times and based on the structural characteristics (chromophore groups) present in the KM-34. This compound could reduce the RL generated in the Fenton-Habber-Weiss reaction, since the phenolic compounds behave as excellent electron donors (Vermerris and Nicholson, 2006). On the other hand, the chelation of metals such as iron through the catechol groups and unsaturations present in the molecule (Perron and Brumaghim, 2009) in addition to the inactivation of $H2O2$, could avoid the catalysis of the mentioned reaction. If, after coordination of the metal, it remained catalytically active, the radical would form in the vicinity of the polyphenol and would be immediately sequestered. A growing number of studies show that the catecholic metal-polyphenol interaction increases the antioxidant and cytoprotective capacity of the latter, mainly because the ligand acquires a new redox center that mimics antioxidant enzymes such as SOD (Pardo, 2007; Núñez et al., 2011).

The fact that KM-34 offers cytoprotective effects at concentrations as low as and even close to the total protection value suggests that this compound could also act by other more efficient molecular mechanisms such as the modulation of gene expression proposed for other agents Binders with antioxidant properties such as DFO, which inhibit NF-κB activation and stabilize HIF-1α, thus enhancing cellular survival responses (Kooncumchoo, 2005; Harten et al., 2010). If this latter mechanism could be properly tested for KM-34, it would be of great relevance for the use of this polyphenol in in vivo systems, considering that the antioxidant effect based only on the sequestration of reactive species, could not Be sufficient to prevent oxidative damage to high concentrations of cell biomolecules (Halliwell et al., 1991). Iron levels with catalytic capacity in the formation of ERO (bound to citrate, ATP and other low-weight molecules), even in situations of abnormal accumulations of iron, hardly exceed 1-2 μM, concentrations that can be chelated by Polyphenols (Halliwell et al., 1991).

In light of the results obtained, it would not be utopian to think of deeper studies with a view to the future implementation of this compound in the therapy of pathological processes related to iron overload and oxidative stress such as Parkinson's disease, Alzheimer's, Amyotrophic Lateral Sclerosis, ischemia, among others.

Example 9. AntiParkisonian Activity of the KM-34

In order to proceed to unilateral dopaminergic denervation of the striatum (right hemisphere), the rats were anesthetized with Cloral Hydrate [0.4 g/kg body weight, ip, Merck (Darmstadt, Germany)] and placed in a frame designed for Stereotactic surgery (Stoelting Instruments, USA), injecting the neurotoxin 6-OHDA-HBr (8 μg/3 μL saline solution into the substantia nigra pars compacta right), which also contained 0.2 mg/ml ascorbic acid As antioxidant). The coordinates were calculated using Bregma's reference point according to the Paxinos and Watson atlas: AP: −4.4 mm; ML: 1.2 mm; DV: 7.8 mm and Incisive Bar: −2.4 mm below the interaural line. Once in place, the neurotoxin was injected slowly, at a flow rate of 1 μl/min, with a Hamilton syringe (5 μl), which was held in situ for 5 min. After the injection is complete.

IV. Behavioral Tests

A. Cylinder Test

In this test the rat is placed inside a cylindrical transparent acrylic 20 cm in diameter and 30 cm high, which does not allow the animal to reach the edge. The cylindrical shape favors the innate conduct of vertical exploration of the wall with the anterior limbs by placing the rat in a location unknown to it. After placing the animal quantifies the amount of touches made by the animal with both front legs, right or left up to a total of 20 touches per animal on the wall of the container. Animals unilaterally damaged with 6-OHDA tend to use the contralateral paw less to the damage, in our case the left paw. The % of asymmetry presented by each animal is quantified through the following formula (% toques ipsilateral) − (% toques contralateral) = (% Asimetria)

B. Exploratory Activity

In order to evaluate the vertical exploratory activity of the animals, the test of exploratory activity was used, the animal was placed in a clear plexiglass cubicle with dimensions of 41×41×33 (h) cm, (UGO BASILE, Multiple Activity Cage Cat. 47420). The cubicle rests on a sturdy base made of black plexiglass, provided with four vertical steel bars with steel notches so that the horizontal/vertical detection systems are correctly fixed. Sensors are IR light emission systems capable of recording the movements of animals in a way, ie vertical scanning. Data is monitored on a computer. The animal is placed in the center of the box, so that it explores the same. The box is placed in an isolated room of the investigator and the ambient noises, in addition to little illumination, for a period of 5 min. The investigator takes the number of times that the animal explores vertically the walls of the box, being interrupted the light beams of the sensor of the box.

Results

Neuroprotective Effect of KM-34 in the In Vivo Model of Parkinson's Induced by the Neurotoxin 6-OHDA The animals treated with the dose of 2 mg/kg and 1 mg/kg had a % asymmetry equal to the animals (healthy) animals, when they were evaluated in the test of the cylinder, thus the animals were not treated with the dose of 0.5 Mg/kg KM-34. The animals of the control group (6-OHDA) that did not receive the treatment, when evaluated in the cylinder test, were not able to use the leg contralateral to the 6-OHDA induced damage, causing a great denervation of the cells Dopaminergic substances present in the substantia nigra, therefore they presented a % of asymmetry so high. As the dose of the compound is increased the animals recover from the damage until reaching a maximum neuroprotective effect in the group treated with 2 mg/kg, being statistically significant with respect to the control damage. Animals treated with 0.5 mg/kg showed no statistically significant difference with respect to the damaged group without treatment, although a certain tendency to decrease the damage was observed. The animals in the vehicle group did not present any damage (FIG. 9).

On the other hand, the vertical exploratory behavior evaluated in the exploratory box did not show statistically significant differences of the 0.5 and 1 mg doses with respect to the damaged animals, but this was not the case for the animals treated with the maximum dose where Showed statistically significant differences with respect to damaged animals and showed no differences with respect to the vehicle group. There is a tendency to increase vertical exploration in the three doses evaluated as the dose of KM-34 increases, being maximum for the dose of 2 mg/Kg of KM-34, FIG. 10.

Example 10. Anti-Dementia Activity

The model of dementia induced by scopolamine has been widely reported for the search for effective compounds in the treatment of different types of dementia, including Alzheimer's disease. Results of the KM-34 evaluation in this model demonstrate the neuroprotective properties of this molecule in the treatment of dementias.

Experimental Design

In in vivo models, KM-34 was administered orally (p.o) at a rate of 4 mL/kg body weight. Doses of 2, 4 and 8 mg/kg were evaluated as acute administration 90 minutes before the start of behavioral tests. For administration the compound was suspended in carboxymethylcellulose (CMC) 0.05%. Scopolamine bromide was dissolved in 0.9% saline solution and administered intraperitoneally as a single dose (1 mg/kg, 4 mL/kg body weight) 30 minutes prior to the initiation of the behavioral tests.

The animals were randomly selected and divided into 5 experimental groups with different treatments (n=7, per group): control group (CMC and saline), vehicle group (CMC and scopolamine 1 mg/kg), KM-34 (KM-34 4 mg/kg and scopolamine 1 mg/kg) and (KM-34 8 mg/kg and scopolamine 1 mg/kg).

Behavioral Studies

Labyrinth in T. Spontaneous Alternation

The evaluation of the spontaneous alternation behavior in the T maze was carried out following the methodology proposed by Capurro et al. (Capurro et al., 2013). This essay consisted of a single section that began with a forced-choice entry, followed by 14 free-choice entries to either the left or right labyrinth arms. At the first entrance, the access to the right arm of the labyrinth was closed, forcing the animal to the open (left) arm. Subsequently, the animal was allowed to freely explore the labyrinth and chose which arm to enter, right or left, in 14 opportunities. Between each choice the animal was returned to the starting position (end of the long arm of the T), where it was confined for 5 seconds. The series of entries to each arm was recorded and the percentage of alternation was calculated as: (number of alternations performed/total of possible alternations)×100. This test was performed 90 and 30 minutes after the administration of JM-20 and scopolamine, respectively.

Object Recognition

This trial was conducted as proposed by Capurro et al. (Capurro et al., 2013), in an open field, on two successive days. On the first day, the animals were adapted to be examined for 3 minutes in 2 sections. On the second day, training and assessment of learning were performed in two stages of 5 minutes each, Test 1 (P1) and Test 2 (P2) respectively. Before initiating P1 the animals were administered with JM-20 and scopolamine, 90 and 30 minutes before, respectively. In P1 the rats were presented with two identical objects, called familiar objects (F). After 30 minutes, P2 was started and the rats were exposed to two different objects: the familiar F and a new object (N). The tests were video-recorded for the analysis of the exploration of the objects, defined by the time of exploration that the animal performs to each object. The discrimination rates between the F and N objects were calculated as: ID=(N−F)/(N+F).

Statistic Analysis

The GraphPad Prism 5.0 program was used for the statistical analysis of the results obtained. The normality and homoscedasticity of the experimental data were checked. An ANOVA (Analysis of Variance, according to English terminology) and Tukey test of multiple comparison were performed to compare between the different experimental groups.

Results

In the T maze, the effect of the different treatments on short-term spatial memory was evaluated. The percentage of alternations correlates positively with the cognitive ability and normal memory of the animals. Administration of 2, 4 and 8 mg/kg of KM-34 (po), 1 hour before inducing a scopolamine cognitive deficit, was significantly (p<0.01) protected from spatial memory damage with respect to non-Treated with KM-34 (FIG. 11).

The effect of KM-34 on episodic object recognition memory was evaluated by the recognition test of new objects in a short-term design. In this test the time of recognition of familiar (F) and new (N) objects during the evaluation phase was quantified, and a discrimination index (ID) was calculated between both objects. A high positive index reflects a good recognition memory of the N object over the F, as observed in the control groups (FIG. 12). An index with values close to zero or negative means that the animals discriminate little between the F and N objects or a greater exploration of the F object than the N. In these tests, it was observed that the doses of 4 and 8 mg/kg of KM-34 (po) were able to revert the affectation on the learning and the memory of term recognition induced by scopolamine. The animals treated with KM-34 were able to discriminate between the previously known and the new object in a similar way as did the control animals of the experiment, and significantly (p<0.01) higher than did animals treated with scopolamine alone (FIG. 11).

These results predict a possible anti-amnesic effect of KM-34. The structural potentialities of KM-34 and the set of pharmacological evidence obtained justify the possibility that KM-34 has neuroprotective effects in the treatment of different types of dementia, including Alzheimer's disease.

Example 11. Anti-Ischemic Activity of the KM-34

The animals were randomly divided into the following groups (n=8 per group): (1) vehicle treated ischemia/reperfusion (I/R) control, (2) KM-34 treated I/R 0.1 mg/kg, (3) I/R treated with KM-34 0.5 mg/kg, (4) I/R treated with KM-34 1 mg/kg, (5) sham-operated vehicle treated and (6) sham—With KM-34 1 mg/kg. In all cases the treatment was administered orally (with an intragastric cannula). For the different doses, the concentrations were adjusted with the aim of administering a constant volume of 10 mL/kg. Immediately prior to use, KM-34 was suspended in carboxymethyl cellulose (CMC) 0.05%.

Induction of Transient Focal Cerebral Ischemia in Rats

Transient cerebral ischemia was performed by the OACM, using the intraluminal filament method. Briefly, the animals were anesthetized with ketamine (75 mg/kg) and xylazine (8 mg/kg). The right common carotid artery was exposed by making a longitudinal incision in the ventral midline of the neck and the common and external carotid arteries were ligated with a 3-0 silk suture. Subsequently, a 4-0 nylon monofilament (Somerville, Brazil) was introduced with the rounded tip and coated with poly-L-lysine (44), up to 18-20 mm in length through the ACI, with the objective of obstructing the origin of the MCA. After 90 min of occlusion, the filament was removed to allow reperfusion. Body temperature was maintained between 36.5° C. and 37.5° C. with a heating blanket. One hour later the rats received a single oral dose of KM-34 (0.1, 0.5 or 1 mg/kg). The animals of the sham group (false-operated) underwent the same surgical procedure but without monofilament insertion. After 23 hours of reperfusion, the neurological deficit was evaluated and the animals sacrificed to determine the infarct volume and perform the behavioral evaluations.

Evaluation of Neurological Deficit

Neurological deficit was assessed according to a six-point scale: 0=no observable neurological deficit; 1=no extension of the left front leg; 2=shifts in circles to the left if the animal is suspended by the tail; 3=spontaneous displacements in circles to the left; 4=no spontaneous motor activity with decreased level of consciousness; 5=death.

Measurement of Cerebral Infarct Size

Cerebral infarction was determined by staining with TTC, a colorless compound in solution but which, when reduced by dehydrogenases of functional mitochondria, forms a red brick formazan salt. In this way the tissue that has been damaged by ischemia remains undyed and can be macroscopically recognized.

The animals were anesthetized again after the neurological evaluation and were perfused transcardially with 20 mL of saline at 4° C. The brains were extracted and placed at 0° C. for 30 minutes. Coronal sections of 2 mm thickness were then performed and incubated in a 2% TTC solution at 37° C. for 30 min. The stained sections were fixed in a solution of 4% phosphate buffered formalin and digitized for the determination of infarct size with an image analysis system (ImageJ 1.41, National Institute of Health, USA). The edema index (volume of the hemisphere ipsilateral to the OACM/volume of the contralateral hemisphere) and the volume of corrected infarction (volume of the lesion/edema index) were calculated to avoid overestimation of the infarct volume by cerebral edema. Infarct volume was expressed as a percentage of the contralateral hemisphere.

Statistic Analysis

Statistical analysis was performed using GraphPadPrism 5.0 software (GraphPad Software Inc., USA). The data were expressed as the mean±SEM (standard error of the mean). Comparisons between the different groups were performed using simple classification analysis of variance (ANOVA), followed by the Newman-Keuls multiple comparison test. A value of p <0.05 was considered statistically significant. All analyzes were carried out by an investigator who was unaware of the assignments of the experimental groups.

Results

Treatment with KM-34 Reduced the Volume of Infarction and Neurological Deficit Induced by Occlusion of the Middle Cerebral Artery in Rats The model of occlusion of the middle cerebral artery in rats, a reliable and reproducible model that causes a sensorimotor and cognitive deficit widely characterized. The compound was administered orally (using an intragastric cannula) at doses of 0.1, 0.5 and 1 mg/kg, 1 hour after reperfusion. TTC staining demonstrated that KM-34 greatly reduced infarct size (FIG. 13A). Quantitative analysis of these data revealed that the total volume of infarction (expressed as a percentage of the contralateral hemisphere) in the rats treated with 0.5 and 1 mg/kg of KM-34, decreased significantly (p<0.05) Vehicle-treated group (27.5% in the vehicle treated group at 15.7% and 5.3%, respectively) (FIG. 13B). This overall effect is a result of the reduction of cerebral infarct sizes in cortical areas such as subcortical.

In the neurological evaluation, no significant behavioral affections were observed in the sham group (results not shown), whereas in the group not treated with KM-34 and submitted to the OACM a severe neurological deficit was observed (Fig. Rats in this group showed movements in circles, flexion of the forepaw contralateral to the damage and decreased spontaneous movements. Treatment with KM-34 (0.5 and 1 mg/kg) significantly improved (p<0.05) the neurological deficit, which is reflected in the decrease in neurological score. In both cases, the abnormalities in the movement and posture of the rats were lower, suggesting that the decrease in infarct size due to the treatment had a positive effect on the postischemic neurological deficit. On the other hand, the administration of this compound produced no sign of tissue damage or behavioral alterations in the sham group, indicating that the compound has no effect on these parameters under basal conditions (without OACM).

Example 15. Biological Activity of Combinations of Tricyclic Derivatives of the Type Benzodiazepines, Pyridodiazepins and Pyrimidodiazepines Fusioned to Derivatives of 1,4-Dihydropyridines Combined with Phenolic or Polyphenolic Derivatives To demonstrate the superiority of the combination of tricyclic and tetracyclic derivatives of the benzodiazepine, pyridodiazepine and pyrimidodiazepine type fused to 1,4-dihydropyridine derivatives with phenolic or polyphenolic derivatives, with respect to each of these systems separately, cell cultures PC12 exposed to glutamate and hydrogen peroxide damage.

Damage by hydrogen peroxide (radical damage) and by glutamate (excitotoxic), are representative of most vascular and nervous disorders. In both graphs it is observed how the groups treated with JM-20+KM 34 presented a greater percentage of survival than the one shown for each of them by separated. This indicates that the mixture of both compounds is superior in terms of therapeutic effectiveness than when used separately, it also predicts that the side effects (responsible for the withdrawal of many drugs from clinical practice) will be lower when the combination of derivatives Tricyclic and tetracyclic benzodiazepines, pyridodiazepines and pyrimidodiazepines combined with derivatives of 1,4-dihydropyridines with phenolic or polyphenolic derivatives, due to the need to use lower doses to achieve a superior pharmacological effect.

As a model of vascular dementia, the animals (male Swiss albino mice) underwent transient occlusion of the common carotid arteries for 20 minutes and cognitive impairment was evaluated through the Morris labyrinthine assay. The results show that the animals administered with 4 mg/kg of JM-20 (po), 1 hour after reperfusion initiated and during all the days of the test, the escape latency time significantly ($p<0.05$) To animals without treatment. The combination of JM-20 (4 mg/kg)+KM-34 (2 mg/kg) showed an improvement in vascular dementia higher than Tacrin 8 mg/kg. As a model of permanent cortical ischemia, thermo-coagulation of the pials arteries was induced and the percentage of asymmetry was quantified.

FIG. 14 shows how the combination of JM-20 (4 mg/kg)+KM-34 (2 mg/kg) decreases the asymmetry of the injured animals more potently than each of the compounds separately.

For dementia and Parkinson's, the combination of JM-20+KM-34 also significantly potentiated the neuroprotective power of each of these molecules separately. This allows the use of lower doses to achieve a superior effect and decreases the risk of adverse reactions.

The invention claimed is:

1. Pharmaceutical composition comprising the compound of formula I

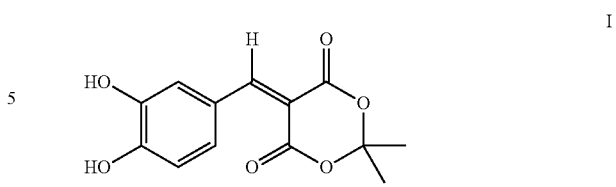

and one or more pharmaceutically acceptable excipients.

2. The pharmaceutical composition according to claim 1 further comprising the compound of formula II

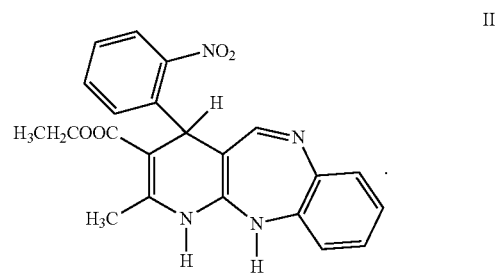

3. The pharmaceutical composition according to claim 2 wherein the compound of formula II is at least in the form of a racemate or in the form of its dextrorotatory or levorotatory enantiomer.

4. A method of treating diseases of the central and vascular nervous system comprising administering a pharmaceutical composition comprising an effective amount of the compound of formula I or a salt thereof:

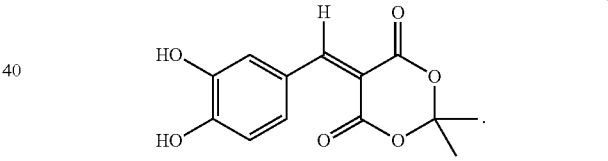

5. The method according to claim 4, wherein the pharmaceutical composition further comprises an effective amount of the compound of formula II or a salt thereof:

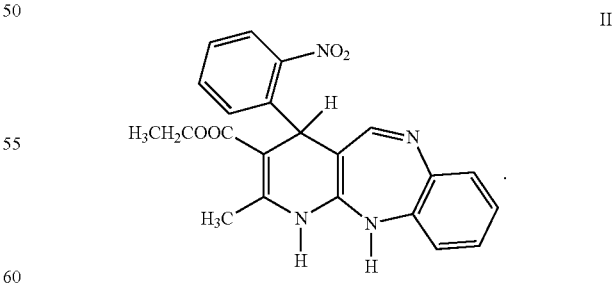

6. The method according to claim 4, wherein the disease of the central and vascular nervous system is cerebral ischemia.

7. The method according to claim 4, wherein the disease of the central and vascular nervous system is Parkinson's disease.

8. The method according to claim 4, wherein the disease of the central and vascular nervous system is related to different types of dementias.

9. The method according to claim 8, wherein the dementia is Alzheimer's disease.

10. The method according to claim 8, wherein the dementia is vascular dementia.

11. The method according to claim 5, wherein the disease of the central and vascular nervous system is cerebral ischemia.

12. The method according to claim 5, wherein the disease of the central and vascular nervous system is Parkinson's disease.

13. The method according to claim 5, wherein the disease of the central and vascular nervous system is related to different types of dementias.

14. The method according to claim 13, wherein the dementia is Alzheimer's disease.

15. The method according to claim 13, wherein the dementia is vascular dementia.

\* \* \* \* \*

UNITED STATES PATENT AND TRADEMARK OFFICE
CERTIFICATE OF CORRECTION

Page 1 of 1

PATENT NO. : 10,722,491 B2
APPLICATION NO. : 16/098683
DATED : July 28, 2020
INVENTOR(S) : Ochoa Rodriguez et al.

It is certified that error appears in the above-identified patent and that said Letters Patent is hereby corrected as shown below:

In the Specification

Column 5, Line 53: now reads "1%"
should read -- % --

Column 6, Line 29: now reads "anal sis"
should read -- analysis --

Column 14, Line 49: now reads ""C" class"
should read -- class "C" --

Signed and Sealed this
Third Day of August, 2021

Drew Hirshfeld
*Performing the Functions and Duties of the
Under Secretary of Commerce for Intellectual Property and
Director of the United States Patent and Trademark Office*